United States Patent
Lee et al.

(10) Patent No.: US 6,347,245 B1
(45) Date of Patent: Feb. 12, 2002

(54) MEDICAL DEVICE ECG MARKER FOR USE IN COMPRESSED DATA SYSTEM

(75) Inventors: Brian B. Lee, Golden Valley; Michael R. Kane, Shoreview, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/353,277

(22) Filed: Jul. 14, 1999

(51) Int. Cl.[7] ............................................ A61B 5/0432
(52) U.S. Cl. ...................... 600/523; 600/509; 607/27; 607/59
(58) Field of Search ................... 607/9, 27, 28, 607/30, 59; 600/509, 510, 521, 519, 523

(56) References Cited

U.S. PATENT DOCUMENTS

| | | |
|---|---|---|
| 4,223,678 A | 9/1980 | Langer et al. |
| 4,407,288 A | 10/1983 | Langer et al. |
| 4,556,063 A | 12/1985 | Thompson et al. |
| 5,313,953 A * | 5/1994 | Yomtov et al. ............. 600/509 |
| 5,331,966 A | 7/1994 | Bennett |
| 5,339,824 A | 8/1994 | Engira |
| 5,404,887 A | 4/1995 | Prather et al. |
| 5,464,431 A | 11/1995 | Adams et al. |
| 5,464,434 A | 11/1995 | Alt |
| 5,518,001 A | 5/1996 | Snell |
| 5,908,392 A * | 6/1999 | Wilson et al. ............. 600/509 |

OTHER PUBLICATIONS

Pace Dec. 1992 vol. 15 (15:588) by Leitchetal Subcutaneous Bipolar "Pseudo–ECG" Recording Using an Implantable Monitoring System and at Chaired Poster Presentation of the North American Society of Pacing and Electrographysiology (NASPE).

Arrthmia Detection Program for an Ambulatory ECG Monitor by Mueller Copyright 1978, ISA ISBN 876645.

* cited by examiner

*Primary Examiner*—George R. Evanisko
(74) *Attorney, Agent, or Firm*—Girma Wolde-Michael

(57) ABSTRACT

A system for recording trigger events and noise in conjunction with the recording of physiological signals is provided for use in an implantable medical device. In one embodiment, recorded trigger and noise data is provided for display to a physician along with reconstructed ECG data to facilitate interpretation of the ECG signal. In one embodiment, digitized ECG samples that are outside of a predetermined range are discarded during the sampling process so that one or more ranges of encoded values are available for use in encoding noise and trigger information. This non-physiologic data may be limited in size to individual point values of the ECG signal.

20 Claims, 17 Drawing Sheets

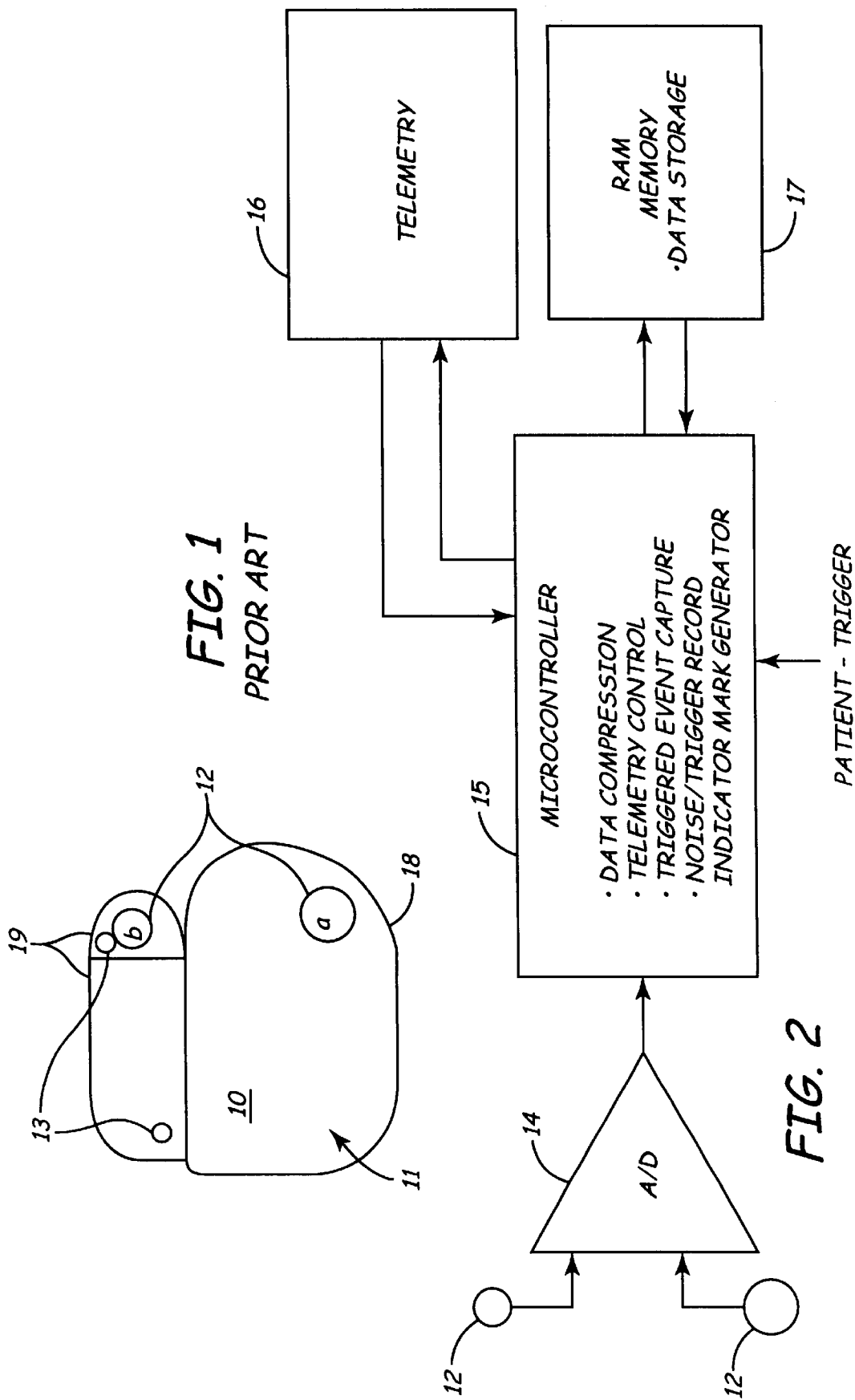

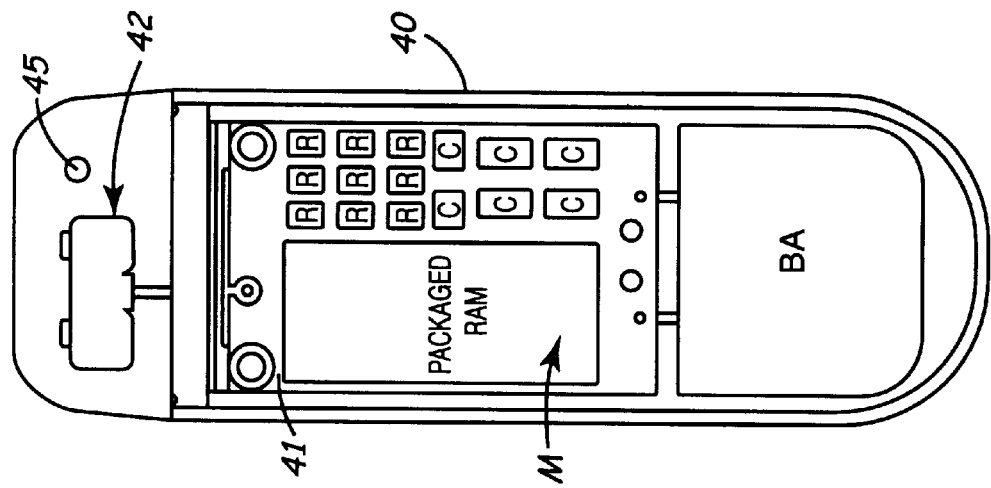
FIG. 4C
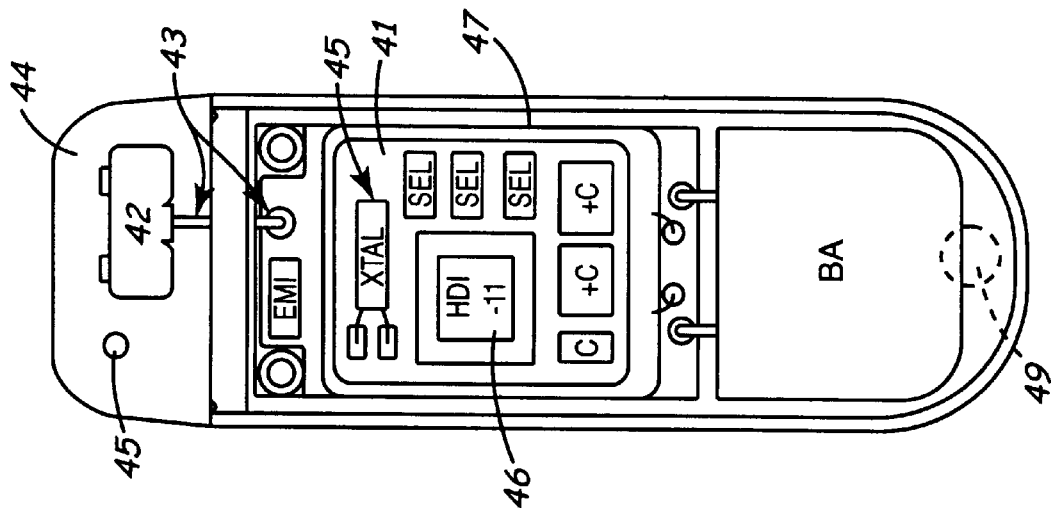
FIG. 4B
FIG. 4A

△=ACTIVATION POINT

MEDICAL DEVICE ECG MARKER FOR USE IN COMPRESSED DATA SYSTEM

FIELD OF THE INVENTION

This invention relates to a device for monitoring physiological signals of a body; and, more particularly, relates to an implantable monitoring device for sensing and/or recording physiologic events with minimally invasive intrusion into the body, but which can be used with various implantable devices.

BACKGROUND OF THE INVENTION

In using implantable medical devices for recording and interpreting ECG or other physiological data, various other non-physiological signals can be recorded and used to interpret the physiological signals. For example, an automatic trigger signal used to activate data storage, or the noise present when the physiological signal is recorded can be useful in later interpreting the data record. Such non-physiologic signals can also be used to eliminate false indications of medical conditions, and to discover actual problems that would otherwise not be identified. This is particularly true when recording far-field electrogram data, since considerable noise is generally present, and the later interpretation of such signal data will be aided by storing this contemporaneous noise. For instance, in devices that utilize R-waves as a trigger event, it is of particular importance to record contemporaneous noise that may have served as a false trigger. Additionally, in devices wherein storage of signals is patient-activated, it is desirable to store and identify the patient-activation signal as the trigger event.

In the monitoring of long-term ECGs to diagnose intermittent heart irregularities, syncopal events, and other physiological conditions, minimally invasive monitors like the Reveal (TM) electrocardiogram event recorder manufactured by Medtronic, Inc. have proven to be useful. However, particularly when the device employs automatic arrhythmia detection triggers to activate the storage of a segment of the ECG, the presence of noise in the ECG signal channel may trigger activations of recordings inappropriately, causing the device memory to become full of unwanted or redundant portions of the cardiac electrogram which may be of little to no use in diagnosing the patient condition. Moreover, such noise makes interpretation and diagnose of the signal difficult.

Several problems exist with storing information related to the noise and/or trigger event associated with a physiological signal. For example, the amount of available storage must be considered. A separate memory or at least a separate location in memory from the ECG storage area may be required. Additionally, some mechanism is needed to identify which marker was associated with any given segment of ECG data storage.

An additional complexity can be found in the limitation on the nature of the data available to store electrogram data samples, especially when, for one example, the sample rate produces more electrogram features than are stored via a lossy data compression technique in long term monitoring devices, a process relied upon to save memory and achieve sufficient data storage capacity to assist the physician in evaluating a long term ECG.

Monitoring can be done using implantable pulse generators such as pacemakers and other heart stimulating devices or devices with leads in the heart for capturing physiologic parameters, including the ECG. However, the expense and risk from implanting a pacemaker or changing out one without these functions is something both patients and physicians would prefer to avoid. Such devices, in addition to performing therapeutic operations, may monitor and transmit cardiac electrical signals (e.g., intracardiac electrograms) to external diagnostic devices typically with leads fixed in the patient's heart, to observe electrical activity of a heart. It is common for implanted cardiac stimulation devices to send intracardiac ECG signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

U.S. Pat. No. 4,223,678 to Langer et al., incorporated herein by reference in its entirety, discloses an arrhythmia record/playback component within an implantable defibrillator. ECG data is converted from analog to digital (AD) form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry.

U.S. Pat. No. 4,407,288 to Langer et al., also incorporated herein by reference, discloses a programmable, microprocessor based implantable defibrillator that senses and loads ECG data into a memory via a direct memory access operation. A processor analyzes this ECG data in the memory to detect the occurrence of an arrhythmia event afflicting a patient's heart. Upon such an event, the defibrillator may generate a therapy to terminate the arrhythmia event and store the ECG data sequence of the event, for transmission to an external monitoring device and later study. In normal circumstances, when no arrhythmia event is occurring, the defibrillator continuously overwrites the ECG data in the memory.

U.S. Pat. No. 4,556,063 to Thompson et al, also incorporated herein by reference, teaches a pulse interval telemetry system capable of transmitting analog data, such as sensed intracardiac electrogram signals, without converting analog data to a digital numeric value. The telemetry system is capable of sequentially transmitting both digital and analog data, individually and serially, in either an analog or a digital format, to a remote receiver. The features and capabilities of such pacemaker/defibrillator devices are now well known, but the problems in long-term monitoring for events and adequate recordation and interpretations of noisy excessively triggered records remain.

An additional implantable arrhythmia monitoring system is described in an article in the December 1992 Vol. 15 edition of PACE (15:588) by Leitch et al. In that article, a feasibility study for implantable arrhythmia monitors describes the use of subcutaneous, bipolar "pseudo-ECG" recordings.

U.S. Pat. No. 5,404,887 to Knowlan et al. describes a leadless implantable sensor for cardiac emergency warning that detects heart events through impedance measurement sensed using a coil. A similar system is disclosed in U.S. Pat. No. 5,313,953 to Yomtov et al., incorporated herein by this reference, which describes a large but leadless implant device. With sufficient hardware and connections to the body, numerous other physiologic parameters may be sensed as is disclosed in U.S. Pat. No. 5,464,434 issued to Alt and U.S. Pat. No. 5,464,431 issued to Adams et al., both incorporated herein by reference.

When using the above-described monitoring systems, it may be difficult to determine which type trigger event initiated storage of an ECG segment. The difficulties are exaggerated by the presence of interfering signals, or, in other cases, by the absence of some interfering signals that have been removed by filtering techniques or other antinoise responses. Moreover, with subcutaneous, or far-field electrodes, ECG signal amplitude may vary greatly with mere change in patient posture, making it difficult to assess whether the recorded signal is a real arrhythmia, or an artifact of poor detection As noted above, this is particularly true when the ECG is reconstructed from a compressed electrogram data.

Therefore, there remains a need to indicate the type of noise that is present in a particular ECG segment, and to do so in an efficient manner within the constraints imposed by the limitations of inexpensive devices with limited communications capacity, battery strength, memory capacity, and having limited time to communicate with external devices, and wherein the storage of the signal is complicated by the use of data compression techniques.

SUMMARY OF THE INVENTION

A system and method for storing and communicating information regarding the type of conditions that existed contemporaneously with the recording of an ECG signal is described. As discussed above, during the recording of ECG segments, a variety of information is lost in the normal use of subcutaneous and other ECG monitors. This information includes both trigger events, and/or non-physiologic noise conditions present when the ECG signal is being recorded. According to one aspect of the invention, this information may be captured with the ECG signal and made available to the clinician as screen data or on an electrocardiogram tape recording, for example. This information is stored in a manner that accommodates the nature of the data compression and data communication requirements of the medical device.

According to one aspect of the invention, the type of trigger event that occurred is indicated. In one embodiment, the trigger event may include automatic events such as a Bradycardia, a Tachycardia, or an Asystole event. In another scenario, the trigger event may be a patient-initiated event. This type of stored trigger information may be useful in determining whether the device is functioning properly, as well as providing some redundancy to the vial examination of the reconstructed electrogram segment.

According to another aspect of the system, noise is recorded with the physiological signal, including noise caused by Electronic Article Surveillance (EAS), Electro-Magnetic Interference (EMI) noise, ElectroMyographic (EMG) noise, spurious electrode/tissue movement, pacing spikes, defibrillator spikes, and so forth. A series of filters or filter taps can be used, together with digital signal processing if desired, to determine the nature of these noise signals as they are occurring.

The noise may be categorized in preferred embodiments by using knowledge about the temporal frequency characteristics of the noise. For example, EMG noise is broad band and can be characterized by broadband filters. As another example, pacing and defibrillator spikes are generally high voltage and current and of regularized or expected duration. EMI is generally high frequency and appears in bursts.

According to another aspect of the invention, recorded noise pulses may be used to logically reject future noise present in the high-level arrhythmia detection logic that may be used to automatically trigger an electrogram storage period.

In one embodiment of the invention, the system stores information about other indications of physiologic condition which either contributed to the trigger event, or occurred contemporaneously with the trigger. Whether the trigger is manually-activated or automatic, such information can provide useful information when diagnosing the stored electrogram.

A wide variety of useful adjunct sensors including sensors for edema, pressure, temperature, cardiac output, blood flow, oxygen saturation of the blood, pH, ischemia in the heart, motion or activity, and other sensors may be used with the inventive system. The combining of contemporaneous information from such sensors with triggered electrograms enhances the ability to diagnose the electrogram. It should also be noted that the data can be stored in parallel, if desired, such that two memory buffers can be filled, one with the ECG data and one with the sensor data. This could be particularly advantageous for a pressure wave signal, for instance.

In one embodiment, the information that is recorded in real-time while the ECG signal is being monitored is stored in the ECG memory area as a set of coded markers within the data itself. These markers, which are set to predetermined, off-limit values, replace data points in the compressed and sampled signal.

In the system for retrieval of the ECG segment for display, an interpretive processor in the external device provides an indicator marker in the electrogram where the trigger occurred or where the measurement of the sensor took place. Although when compressed data is stored, some quality in the reconstructed ECG signal may be sacrificed by the recording of the marker indicators, the diagnostic value of this additional marker information compensates for this information loss. In one embodiment, an interpretive processor can complete the ECG display using an intelligence algorithm.

If noise is present in the input signal, the device can respond by eliminating R-wave detection signals or by modifying the patterns of acceptable auto trigger responses to apparent R-waves in the presence of noise, which may affect which segments of the ECG will be recorded. In such cases, no data may be stored if the trigger event does not occur.

According to yet another aspect of the invention, other data may be captured along with noise, including additional physiologic condition sensor data, apparent R-waves which may be used for the arrhythmia triggers, indications of losing contact with the body by the electrodes, detecting pacing pulses, defibrillation pulses, low battery and other internal to the device conditions and so on. Other types of signals that may be recorded include ElectroMyoGraphic (EMG) noise from muscle activity, artifact noise from electrode motion within the body, loss or change in the electrode/body contact, pacemaker pulses, defibrillator pulses, and Electro-Magnetic Interference (EMI), which can be of a wide variety of types from different sources. Any combination of such data may be stored in various preferred embodiments of the present invention.

BRIEF DESCRIPTION OF THE DRAWINGS

FIG. 1 is an exterior side view of a prior art device.

FIG. 2 is a block diagram of parts of an implantable medical device for use with a preferred embodiment.

DETAILED DESCRIPTION OF THE PREFERRED EMBODIMENT

Figure 3:
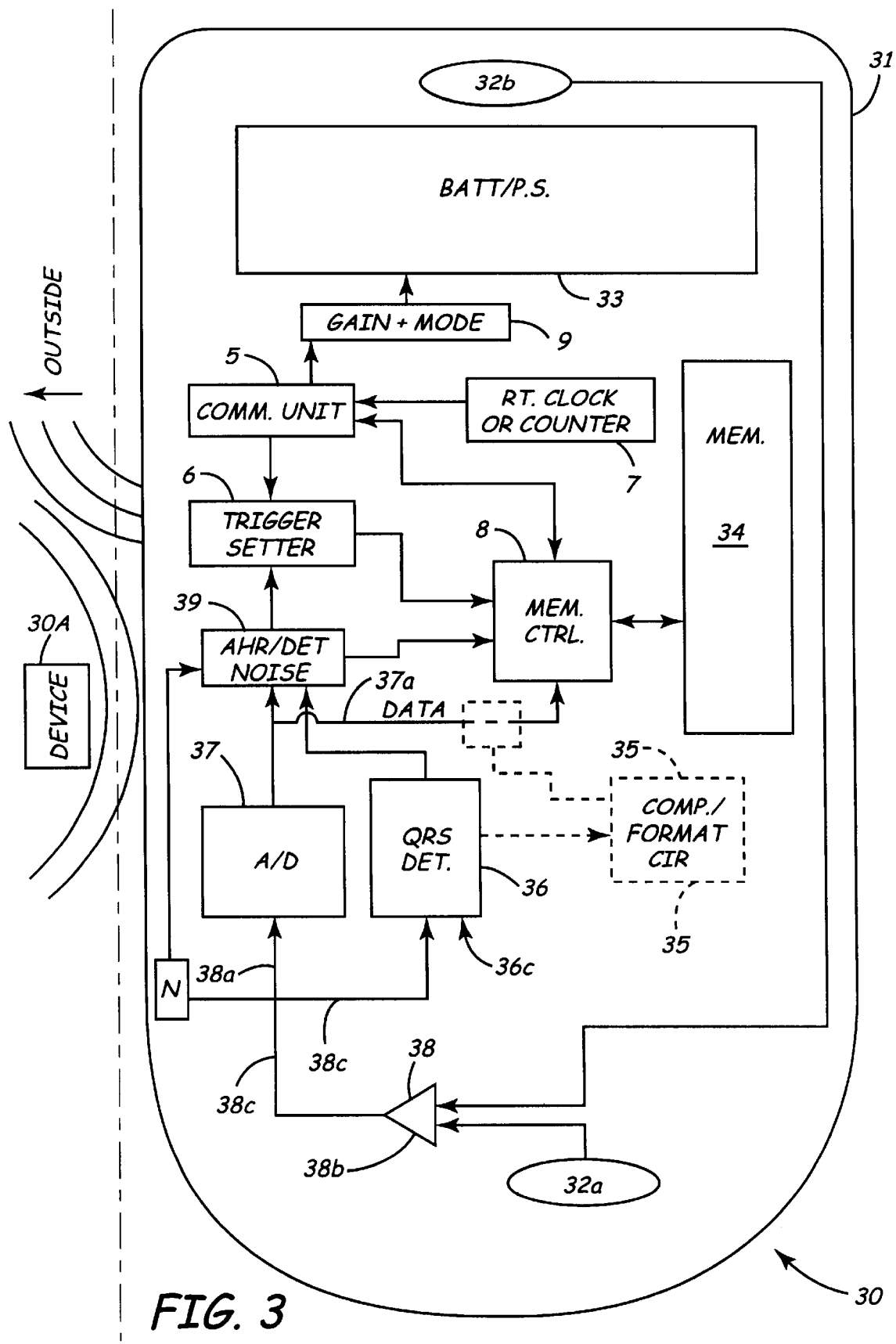
FIG. 3 is a block diagram illustrating the main circuit and assembly of a device in accord with a preferred embodiment.

Prior to Medtronic Reveal (™) implantable ECG monitor, the only consistent use of implantable electrode sensing systems employed leads located in the heart because of the quality of the signal obtained that way. Subcutaneous electrodes, which are located below the skin and produce a far-field electrocardiogram as compared to the intracardiac ECG available through most implantable devices today, have thus only recently been demonstrated to be effective in producing good monitoring devices. These types of electrodes have not yet found large-scale commercial medical success. A well-known example of a system having leads which also contained more than a single electrical contact in the body of the pacemaker was described in U.S. Pat. No. 5,331,966 issued to Bennett et al. incorporated herein by this reference.

Particularly in non-therapeutic devices that merely record physiologic conditions into the physiologically relatively noisy environment of the subcutaneous region, data regarding noise and auto-trigger becomes more important.

FIG. 1 illustrates an early implantable device which appeared at a NASPE (North American Society of Pacing and Electrophysiology) conference as a poster presentation in 1994. The device 10 was provided with two suture holes 13 and two spaced-apart, non-lead or leadless electrodes 12 at one and one-quarter inches distance center-to-center. The device was coated with paralene indicated by arrow 11 so that the only area of exposure on the body of the pacer can 19 is the exposed area at the electrode 12a. The other electrode is a metal plug electrode 12b mounted in a connector block 19.

FIG. 2 illustrates a block diagram of a system, including the same electrodes 12 supplying signals to circuitry inside the housing or "can" 18 (FIG. 1). The circuitry includes an analog-to-digital conversion and amplifier circuit 14. Data from this circuit 14 is provided to a microcontroller 15, which performs data compression, telemetry control, and event capture as may be triggered by patient operation. Telemetry block 16 and RAM memory storage 17 are also provided by this device.

FIG. 3 is a circuit block model 30 is illustrated in an outline of an implantable device having a shell 31, and is of a type that may be used with the current invention.

Electrodes 32a and 32b receive a signal from the body to an input mechanism 38, shown as a differential amplifier for simplicity only. The amplifier provides an output signal to a QRS detector 36 and an AID converter 37, each of which may supply am output signal to an arrhythmia/noise detection circuit 39. In a preferred embodiment, detection circuit 39 supplies the auto-trigger signal to the trigger setting circuit 6.

In the following discussion, it may be noted that the terms auto-triggering and auto-activation and auto-detection are used interchangeably. These terms all refer to the action of storing information in memory based on an automatic response to a change in a measured parameter or count or algorithmic process determination.

Returning now to FIG. 3, the data provided by the analog-to-digital converter may be converted, compressed, formatted and marked or reformulated by circuit 35 before the data is stored in memory 34. Memory control circuits 8 receives input from the A/D converter, with or without conversion by circuit 35, from an auto-triggering determination circuit shown here as the arrhythmia/noise detection circuit 39. The arrhythmia/noise detection circuit may receive input directly from the QRS detector if desired, as well as signals from the trigger setter circuit 6.

The memory controller circuit may compress the electrogram data, preferably using a variation of the tuning point algorithm of U.S. Pat. No. 5,331,966 incorporated herein by reference, although any compression technique may be employed for storing the ECG to memory.

The trigger setter circuit may be controlled by a communications unit 5 which operates to receive and decode signals from outside of the implant 30. These signals may be transferred via a telemetry or other communication circuit by a user. This communications unit 5 may also communicate with the memory controller to request the off-loading of memory data for analysis by an outside device. It may contain an antenna or other transceiver device or circuit to communicate with an outside device such as device 30A. A clock or counter circuit 7 reports the time since start, or real time, to the outside interrogator device 30A contemporaneously with a data off-loading session so that the events recorded in memory 34 may be temporally located.

Alternatives to this overall design may be considered, for example, by using a microprocessor to accomplish some or all of the functions of circuits 6, 8, 39, and 35.

Figure 4:
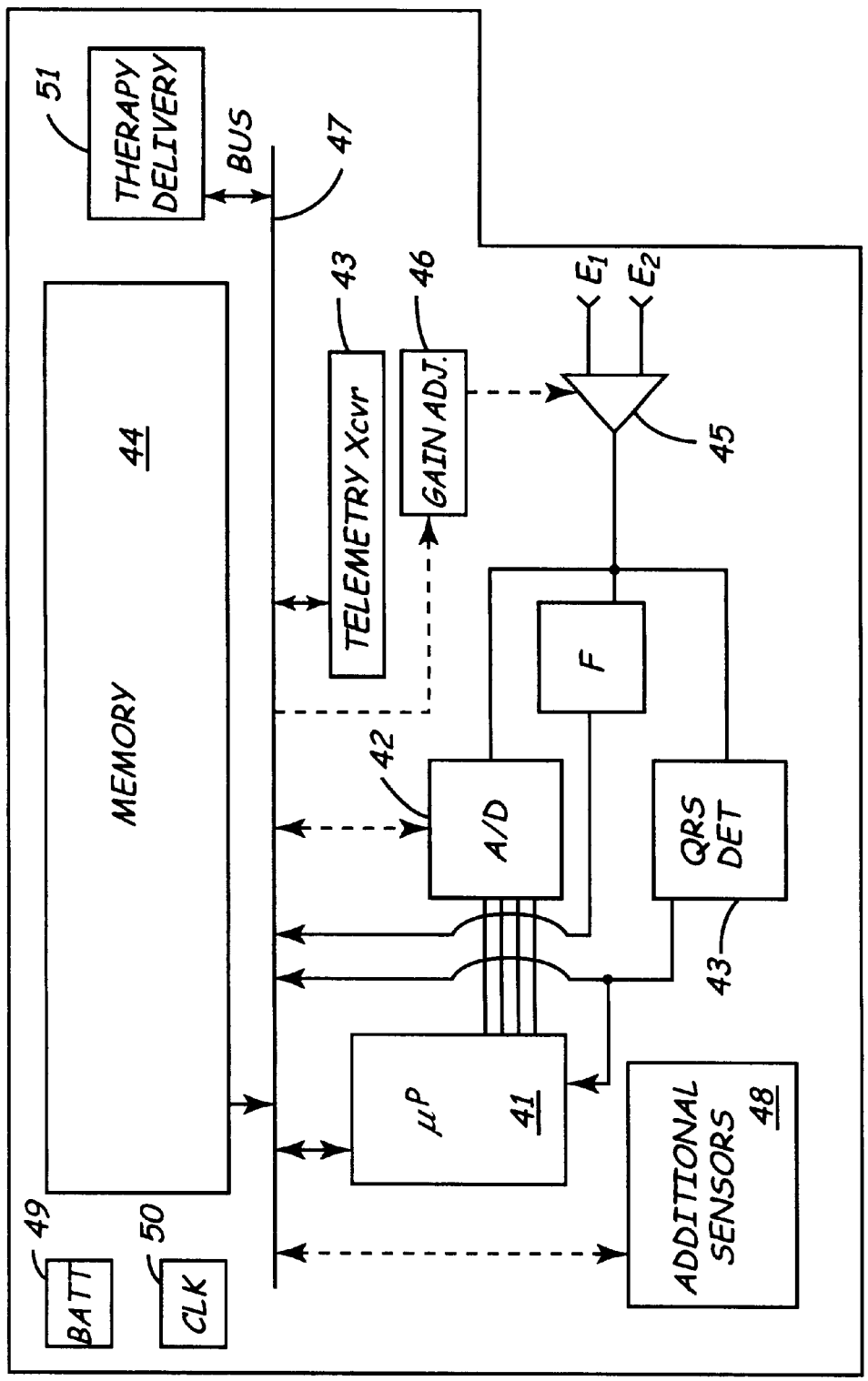
FIG. 4 is a block circuit diagram of an alternative embodiment to that illustrated in FIG. 3.

However, it is believed that such an alternative design will not provide the power and size savings taught by use of the preferred design. FIG. 4 and accompanying description below discloses an exemplary microprocessor-driven version.

FIGS. 4A–C illustrate one preferred embodiment 4 of the invention. This embodiment includes an outer titanium shell 40 and a plastic cap means 44, which together form the exterior of the device. The cap means 44 may be composed of material similar to those used for pacemaker connector blocks. The two electrodes, 44 and 49, provide metal surface contacts to the body. Electrode 49 is formed in a paralene coating over the metal body 40 of the device. The metal electrode 42 is connected via a feedthrough 43 which is itself electrically connected to the circuit board 41. Circuit board 41 contains all the electronics required for the device function and is connected to a battery BA for power. An integrated circuit 46 houses circuitry and intelligence required for the function and the memory M is packaged on the other side of the circuit board.

In this preferred embodiment, the invention uses a communications circuit 45 having a telemetry antenna both to indicate from outside the body that a read out is requested of the device, and for communicating data out from said device. Programming of the device or mode setting will also use the communications circuit 45. In this form, one or more suture holes 45 may be provided through the cap means 44. Electrode 49 is connected by a conductive connection (not shown in FIG. 4) to the circuit board. In this embodiment, the length "l" is substantially longer than the width "w". These measurements can be varied within the constraints described.

The exact sites of implant may advantageously be varied from patient to patient for various reasons apparent to the physician Implant just under the skin may provide a signal that is most free of skeletal muscle myopotential or body movement signal interference.

Referring again to FIG. 3, the external device 30A is preferably a device that is commonly called a "programmer" in the pacemaker art, because its usual function is to communicate with, and to program, implanted devices. Software modifications and modifications to the telemetry system of device 30A to accommodate communication with, and analysis of, data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for mere ECG monitoring and event triggering is minimal, so in the preferred embodiments that only monitor some form of ECG or other limited sensory input, a microprocessor can be eliminated by using particularized functional circuits instead of performing the functions in software.

Turning now to FIG. 4, an alternative form of the implantable monitoring device 40 is illustrated. This device receives input from two electrodes $E_1$ $E_2$ using an input amplifier 45. The output of the input amplifier is provided to analog-to-digital converter (A/D) circuit 42, which provides an input data stream to the microprocessor 41. Additionally, a QRS detection circuit 43 monitors the analog output of amplifier circuit 45, providing an output signal to either the micro processor 41 or the bus 47 as desired. In this simplified device 40, the bus 47 will provide a data conduit for enabling and disabling functions of all circuits attached to the bus, and for providing a means of data transmission between the various circuits components and elements of the device 40. A telemetry transceiver 43 and memory circuit 44 will be able to move large amounts of data in a convenient way along bus 47 as required for the operation of the system. A data compression circuit may preferably be included as part of the A/D circuit. Additional sensor circuits 48 may also provide data to the various circuits through bus 47. Information from the additional sensor circuits, the QRS detector, or the A/D output itself can be processed by the microprocessor to determined if the ECG contains particular kinds of noise.

The circuit may include a filter and characterization circuit F. If so, the device may tap the analog input either before or after the amplifier, depending on whatever filtering might be inherent in the electrode-to-amplifier pathways, to process frequency, duration and amplitude characteristics inductive of particular kinds of noise. The evaluation made by filter and characterization circuit F circuit will preferably be provided as an output in the form of a coded instruction to the microprocessor so that it can be added as an appropriate value to the stored electrogram segments when the instruction is received by the microprocessor. The signal provided by the filter circuit may also be used as an input to help improve arrhythmia detection accuracy. Alternatively, it could be provided to a compression and storage circuit if the ECG signal is provided to the memory through such a route.

A battery or other power circuit 49 is provided along with a clock circuit 50. The clock circuit is necessary to coordinate the transmission of data between the various circuit components and time their functions. Additionally, if desired, a therapy delivery circuit 51 may provide additional functions for the implanted medical monitoring device so that the device may take advantage of the data being gathered to deliver a particular therapy to the patient in a timely manner.

It may be noted that the current invention contemplates modification of any of the following circuits so that these circuits may be used with alternative embodiments such as those that rely on a micro processor controller circuit as in FIG. 4.

Figure 3A:
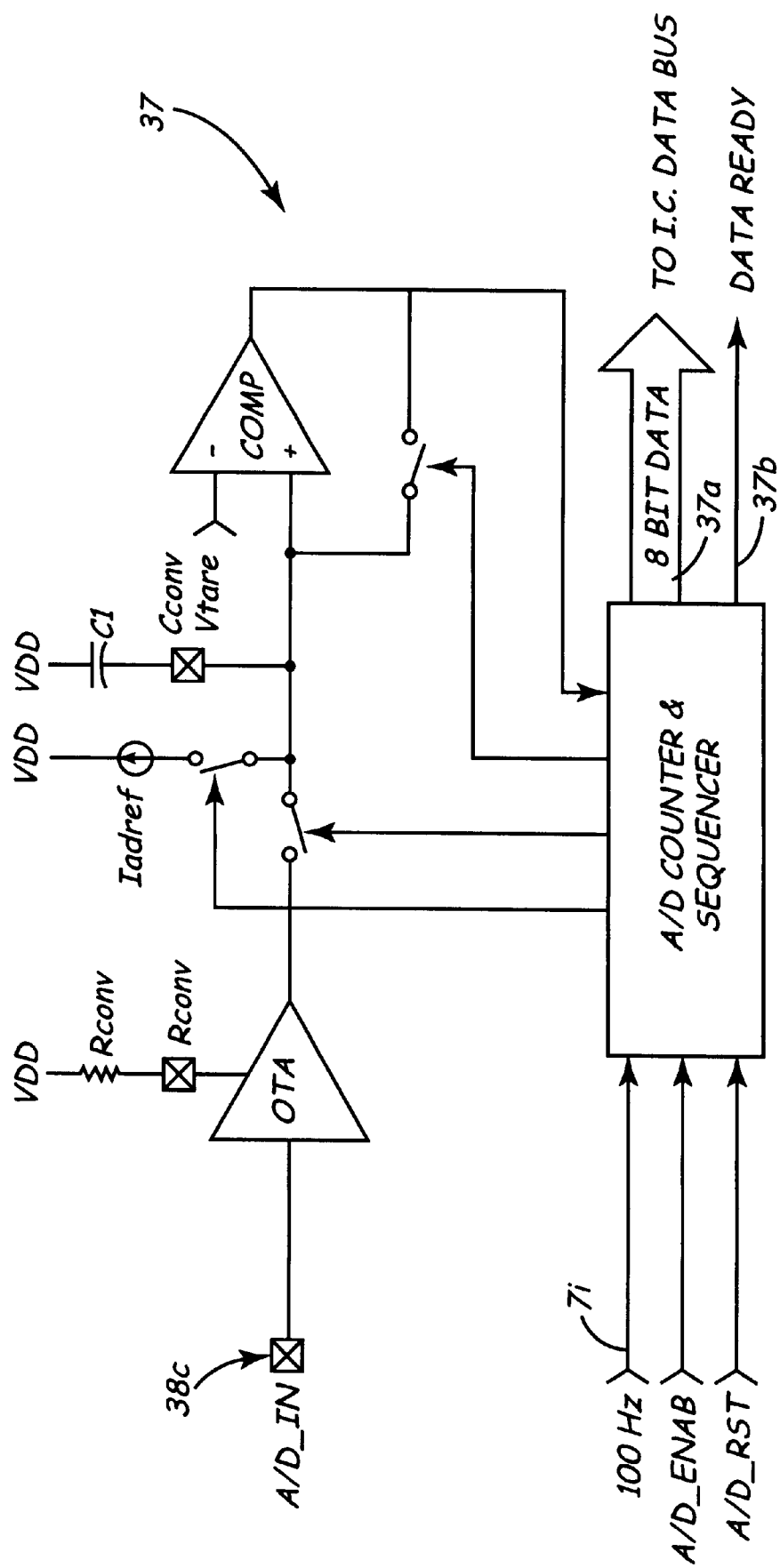
FIGS. 3A–D are block diagrams of preferred embodiment circuits of the implanted device used for monitoring and storing ECGs.

FIG. 3A illustrates a block diagram of an analog-to-digital conversion circuit for use in this invention is shown. The clock input may advantageously use an output from the clock circuit 7, shown input 7i. The input 38c is the analog input signal from input circuit 38, and the converted output is a stream of 8 bit digital data words on line 37a, sequenced by a timing line 37b.

Figure 3B:
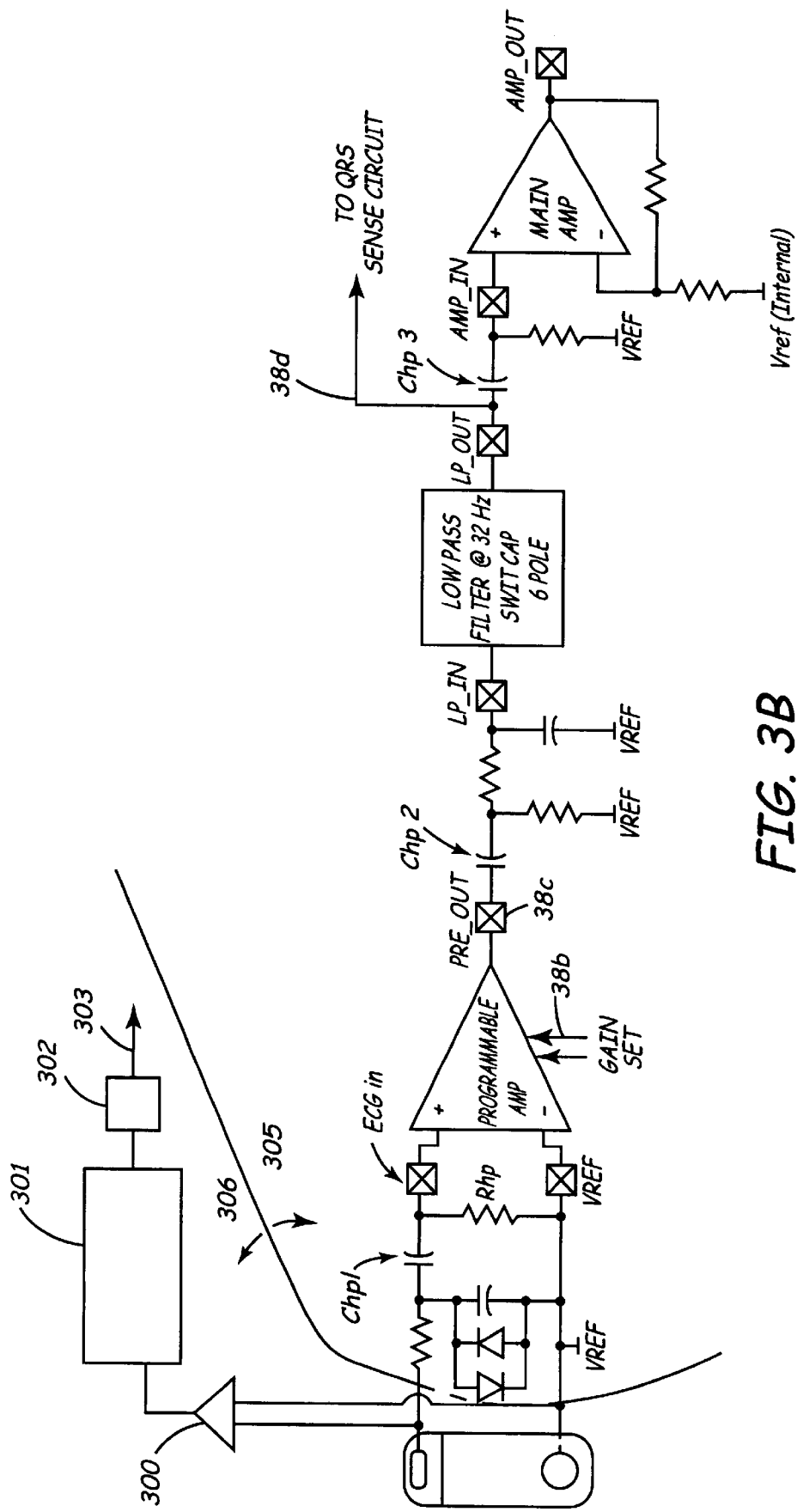

FIG. 3B illustrates the basic components of circuit 38, additionally indicating the input of two gain set bits which can modify the value of the output of the low noise bipolar amplifier for output at line 38c, which after filtering will provide the input to the QRS detector at 38d. In this invention, QRS detection is done on the analog signal, advantageously avoiding more complex detection required after digital conversion for the triggering of event storage. This figure illustrates the preferred embodiment including the tapping of a signal directly from the electrodes to amplifier 300 for determining what kind of noise that may be included in a physiological signal. However, it should be noted that at any stage in the process of producing an output for the QRS detector (38d) or even at the AMP_OUT stage, one could tap off the signal to generate an indication of a particular kind of noise. For example, at the AMP_OUT stage, one could detect pacing spikes, but not most defibrillation pulses, and the EAS and EMI noise signals would likely be lost in the low pass filter 304. Accordingly, since the main path 305 of this circuit 310 is for determining valid QRS signals and providing ECG amplitude values for conversion to digital signals for compression and storage, the alternative path 306 is a preferred approach. In path 306 the signal will be filtered and analyzed appropriately to the particular kinds of noise the device seeks to mark in box 301, and the output will be collected and digitized in box 302 for processing and storage. Preferably, the signal will be stored in the electrogram or ECG signal storage area of the memory.

Figure 3C:
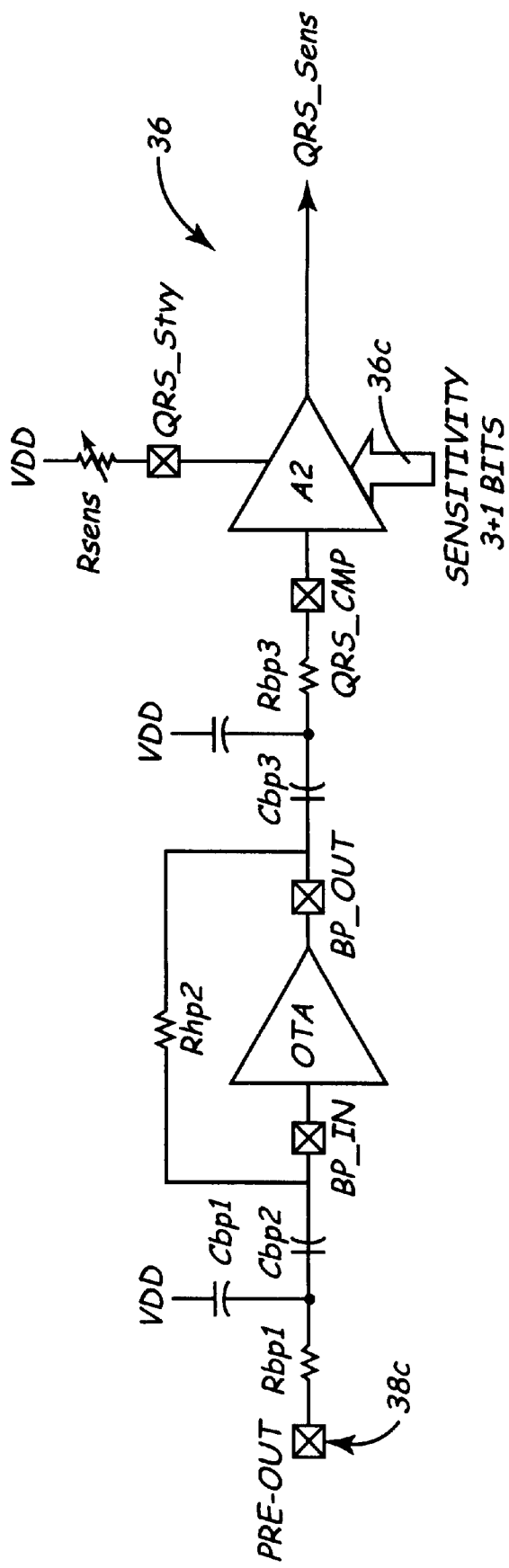

FIG. 3C illustrates a QRS detect circuit 36 having a second-order bandpass filter with a center frequency preferably in the 20–25 Hz range. It includes a transconductance amp A1, summing amp/comparitor A2 and resistors Rbp1–3, capacitors Cbp1–4 and selectable resistor R sense connected as shown. R sense is preferably adjusted during manufacture. Additional control is provided for QRS sensitivity at line 36c, since the gain is detectable for this input.

Figure 3D:
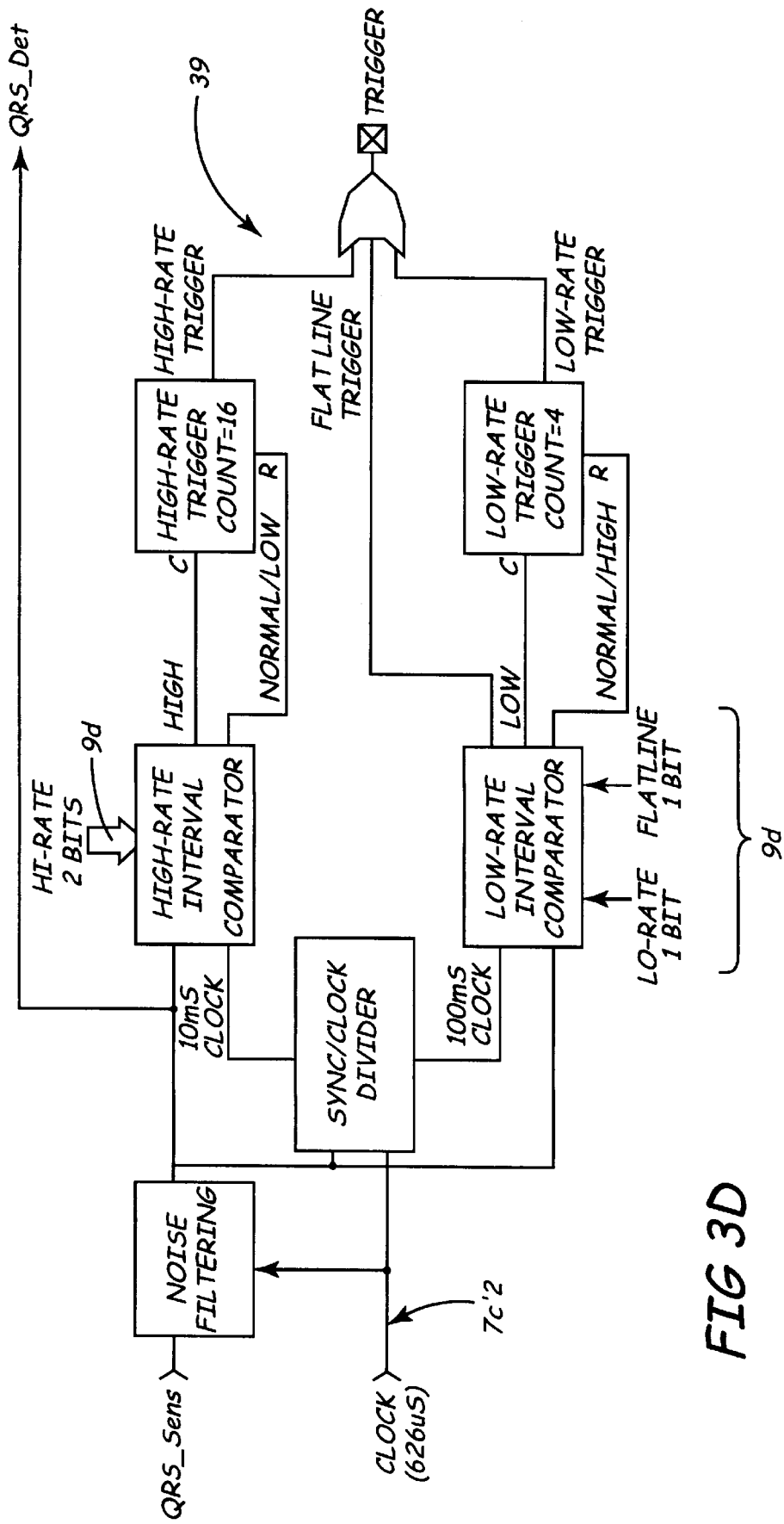

A simple arrhythmia detection circuit 39 is included with this preferred embodiment, and illustrated in FIG. 3D. The output from circuit 36 is monitored at a noise filtering circuit. A preferred embodiment of the circuit is described in more detail in co-pending application Ser. No. 09/353,167 filed on even date herewith and incorporated by this reference, although it will be understood any suitable filtering technique can be used. The preferred circuit utilizes a 180 ms accommodation period controlled by a clock input 7c'2. In one embodiment, a high rate can be selected from four possible high-rate triggers, with two selection bits dedicated to do so at input 9d. The low and flat-line trigger rates each have one bit to turn them on or off provided by inputs 9d. These inputs designated 9d may be provided by a register that holds the gain, the mode, and the rate settings, illustrated as register 9 in FIG. 3. Such features may be programmable through communication with the implanted device by an external device. One preferred timing for the high rate triggers is 140, 162 and 182 beats per minute, requiring 8 consecutive beats at such a rate to initiate the trigger. In one embodiment, seven different physician-selectable triggers are provided for tachyarrhythmia, each utilizing sixteen consecutive beats at the selected rate, but there is room for variation in these choices. Additionally the trigger may be disabled.

The low rate counter/comparator may be programmable to detect low rates of 40 or 30 bpm, requiring 4 consecutive low rate intervals to trigger. Additionally a flat-line trigger can be set to occur after 3 or 4 and one half seconds of no QRS detection.

For embodiments that include more sensors and/or electronics, an additional sensor could be added to benefit the patient. One particularly useful sensor would be an activity sensor based on a single or multi-axis accelerometer, which indicates the level of patient activity and orientation. By checking for output that indicates the occurrence of a VVS (VasoVagal Syncope) episode, (for example, the patient falling from an episode) such an addition offers an improved trigger for events that might otherwise be missed by an arrhythmia detector set up like in FIG. 3D. Such a sensor trigger could replace the circuitry of FIG. 3D.

Additional circuitry and sensors may be provided to determine the presence of Electronic Article Surveillance (a signal used to protect stores from shoplifting), EMG, EMI, pacing spikes, defibrillator pulses, edema, pressure, temperature, cardiac output, blood flow, oxygen saturation of the blood, pH, ischemia in the heart, and so forth. Sensors and interpretive circuitry for all of the foregoing are presently known. The output from any of these sensors and other such as sensors for sensing chemical markers, may be used to trigger ECG storage, storage of data from the sensor itself, or just markers indicating which sensor tripped the trigger for ECG storage, as desirable in any particular situation.

Additional circuits may also be provided to support additional functions if desired. Such additional circuits may support oxygen sensing, pressure sensing, respiration sensing, and any other kind of sensing that can be demonstrated to have been known for implanted devices. They may each have their own auto-triggers based on sensor output, or depend on manual triggers. Additionally, activity sensing or positional sensing devices can provide additional input for recording and or auto-triggering functions. As new sensors become available they may also be incorporated into these designs. However, in order to reduce size and power consumption, extend the life of the device, and reduce the intrusion into the body of the wearer, such auxiliary circuits should be kept to a minimum.

Of course the inventive features described herein can be incorporated into a pacemaker or ICD or other therapy delivering device, employing therapy delivering features of such devices in conjunction with the data recording features of this invention.

Storing Noise and Trigger Data in ECG

Figure 5:
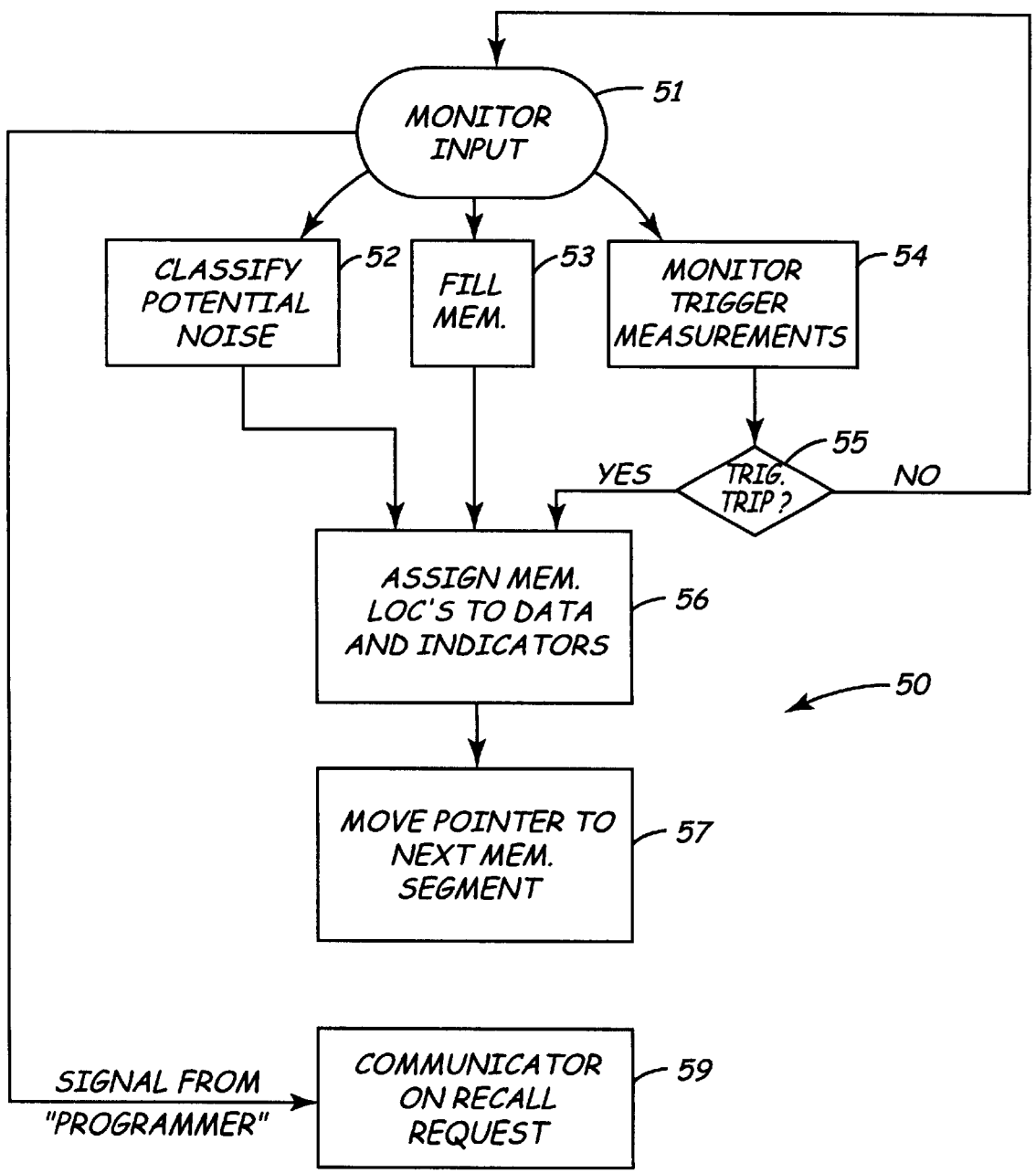
FIG. 5 is a flow chart of a preferred embodiment of the process taught herein.

FIG. 5 is a flow chart 50 of the process by which indicator flags or markers may be included in electrogram data in the memory of the implanted medical device. The implanted medical device, in the preferred embodiment, includes a looping memory electrogram (ECG) storage system that continually monitors the electrogram input in step 51. As it is monitoring this input, it also classifies potential noise in step 52, fills the memory with the current ECG step 53, and monitors the trigger measurements to determine whether an automatic trigger or a patient-activated trigger event has occurred. If it is determined that no trigger event has occurred in step 55, the memory can continue to store signals as may occur using a circular buffer configuration in step 53. Potential noise classification can continue during this time. If however, a trigger event has occurred, or a patient-activated trigger has been set, memory locations become assigned to the ECG data and to whatever indicators will be used in this particular embodiment indicating the nature of the noise present or the kind of trigger event that initiated the data storage, as shown in step 56. In step 57, the memory locations that stored the electrogram signals, trigger event, and/or noise data, is protected from being overwritten by moving a pointer to the next memory section in step 57 and the monitoring process is repeated.

It should be noted with regard to step 56 that there is an upper limit to how much data can reasonably be included in an ECG signal without completely degrading that signal and making it unusable, as well as a reasonable range of amounts of supplemental data that can be included before minimal noticeable degradation takes place. In preferred embodiments, markers are included within ECG data not more than once per cardiac cycle, with samples being taken at 10 mS intervals. Other embodiments could be utilized, such as storing a marker once per second, or once per stored ECG segment, wherein an ECG segment may be several minutes in length. When using a once-per-beat limit, the system would have available a marker data unit at a rate of 180 beats per minute of one data marker per heart beat, or data marker per 30 ECG samples. Reasonable variation on these figures will be apparent to one of skill in this art within the scope of the current invention. The current embodiment limits the inserted data to once per recorded ECG six-minute segment, which is within the range of reasonable reconstruction as discussed above.

If this process is used in the context of a system that utilizes an external device, an additional step 59 is included to transfer the contents of memory to an external device. The external device, which may be a programmer, a receiver/transceiver near the patient, or some other remote device linked to an external receiver/transceiver, will decode and display the transferred data.

Figure 6:
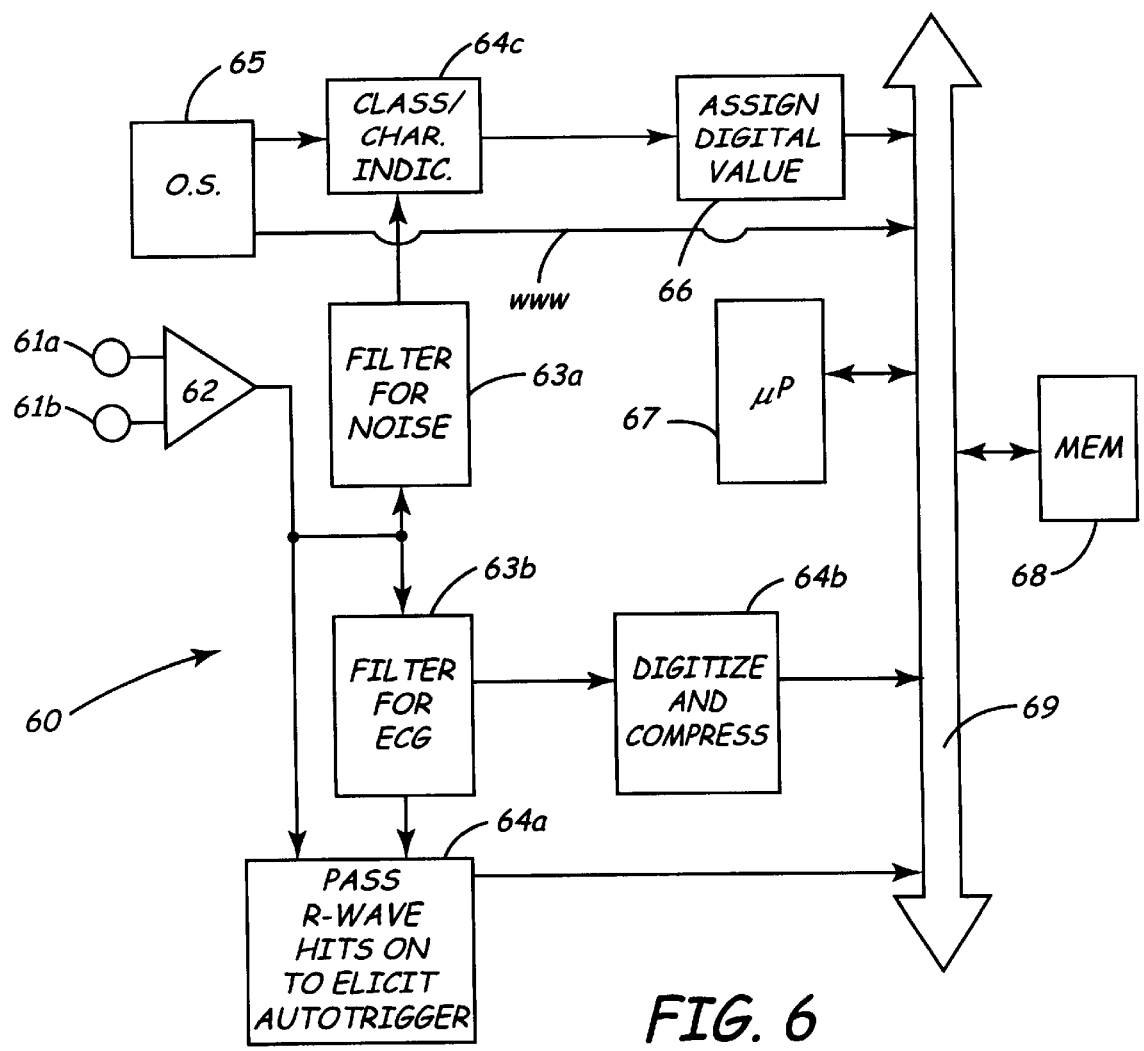
FIG. 6 is a heuristic block diagram illustrating a preferred embodiment.

FIG. 6 illustrates a re-characterization of the functional blocks of the prior FIGS. 3 and 4 as diagram 60. Again, the electrodes 61a and 61b provide signals to the input amplifier 62. Various kinds of filtering schemes may be required for different purposes. Here two filter circuits are indicated as filters for noise 63a and filters for ECG 63b.

In circuit box 64c the characterization of the indication is made based on the input from the noise filters 63a, and also based on input from other sensors if other sensors are included in the device from box 65. A digital value is assigned to the appropriate or highest-priority trigger or noise signal from box 64c in box 66. This is then provided to the microprocessor controlled by a program in memory 68. The filter for the ECG, box 63b, may remove unwanted noise from the ECG signal, which can be filtered out according to a preferred ECG filtering scheme. For subcutaneous monitoring, a system as described in the co-pending application Ser. No. 09/353,167 filed on even date herewith and referenced above is preferred. The filtered signal will be digitized and compressed, if preferred, in blocks 64b and is then provided to the data block 69 in this embodiment. The filtered ECG signal and the raw data signal may be also processed by box 64a which passes R-wave hits as an indicator to illicit auto-triggering based on number of hits per second translated into a heart beat rate. Details of such triggers are plentiful in the prior art and a preferred system is described in the aforementioned co-pending patent application incorporated herein by reference in its entirety.

Although separate memory elements such as ROMs, or separate RAM memory elements could provide the memory storage to provide the programming for the microprocessor 67, it is appropriate for the sake of simplicity to think of the programming as being stored in the same memory 68 into which the digitized and compressed ECG data will be stored to simplify the explanation of a device. Any conventional memory arrangement may be used.

In our preferred embodiment, we store sampled amplitude readings of the electrogram signal, but employ a lossy compression scheme whereby some amplitude measurements are stored, and some intervening measurements are not. A description of an appropriate scheme for the compression of ECG data in our preferred embodiment is described in U.S. Pat. No. 5,331,966 hereby incorporated by reference.

Figure 7:
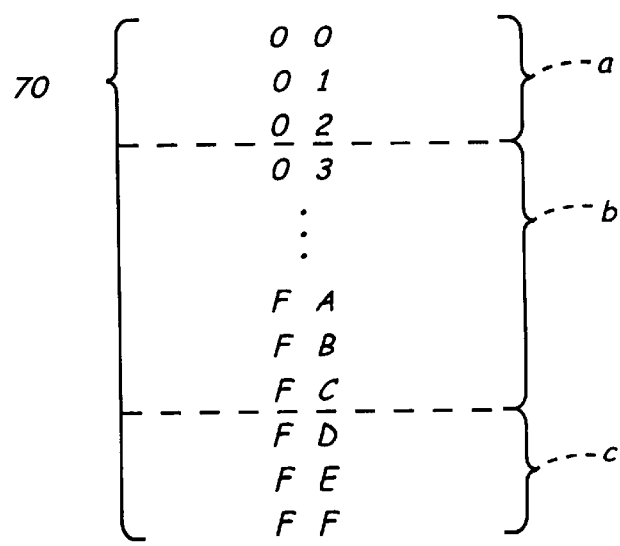
FIG. 7 is a number chart.

Referring now to FIG. 7, this figure illustrates one embodiment in which a 256-level amplitude indication may be presented as a single byte of data. Here, the range of a byte of data is indicated in area 70. The very lowest amplitudes 00–02 hex, shown as area (a), is the low-end of the input amplifiers' range. Likewise, the upper end of the range is at area (c). Accordingly, by retaining only the middle range (b) as good data and discarding the other data located at end ranges 'a' and 'b', the end ranges may be used to encode other signals besides the amplitude of the ECG signal. These signals may be stored in the same memory that stores the ECG signal. There are several reasons for choosing the upper and lower ends of the available range of data for this purpose. For example, not many useful data signals within the QRS complex have an amplitude within the end ranges. Additionally, this design simplifies the design requirements by excluding these values as available outputs from the A/D (Analog to Digital) converter circuit, thus avoiding the necessity of using a digital filter before data is stored to memory. The isoelectric, or near zero values, of the ECG could also provide values of use for recording information other than the ECG in the ECG data storage area, but as just mentioned, this is not preferred since it will add complexity to the design.

Figure 10:
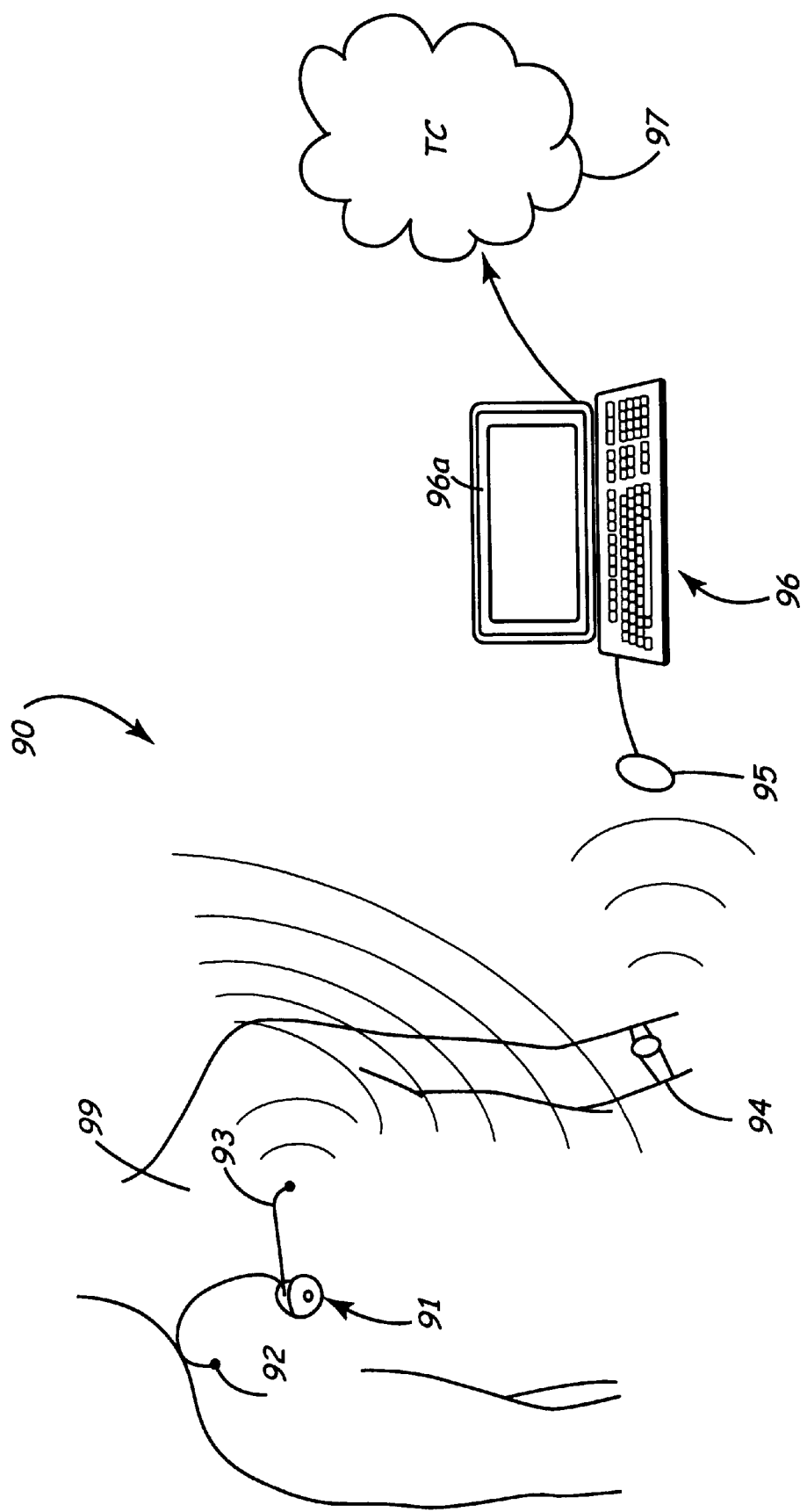
FIG. 10 is a heuristic illustration of a system for use by a preferred embodiment.

FIG. 10 illustrates an electrogram recording implanted medical device 91. Such a device may include leads containing electrodes 92 as well as antenna leads 93. A telecommunication system 97 provides communication between the implanted medical device 91 and external devices 94, 96. Device 94, which may be worn or carried by a patient, can be a repeater for providing additional range to the telemetry signal from device 91 through an antenna or lead acting as an antenna 93 or the device 91 communicate with device 96 through an antenna 95 attached to the external device 96. Most-commonly, this external device is called a "programmer." In any event, in order for the device 96 to correctly interpret a stream of data having amplitude information within it, it is preferred that some of the available byte values at the far ends of the byte value range may be set aside for communicating information other than ECG amplitude values in a manner similar to that discussed above.

Figure 13:
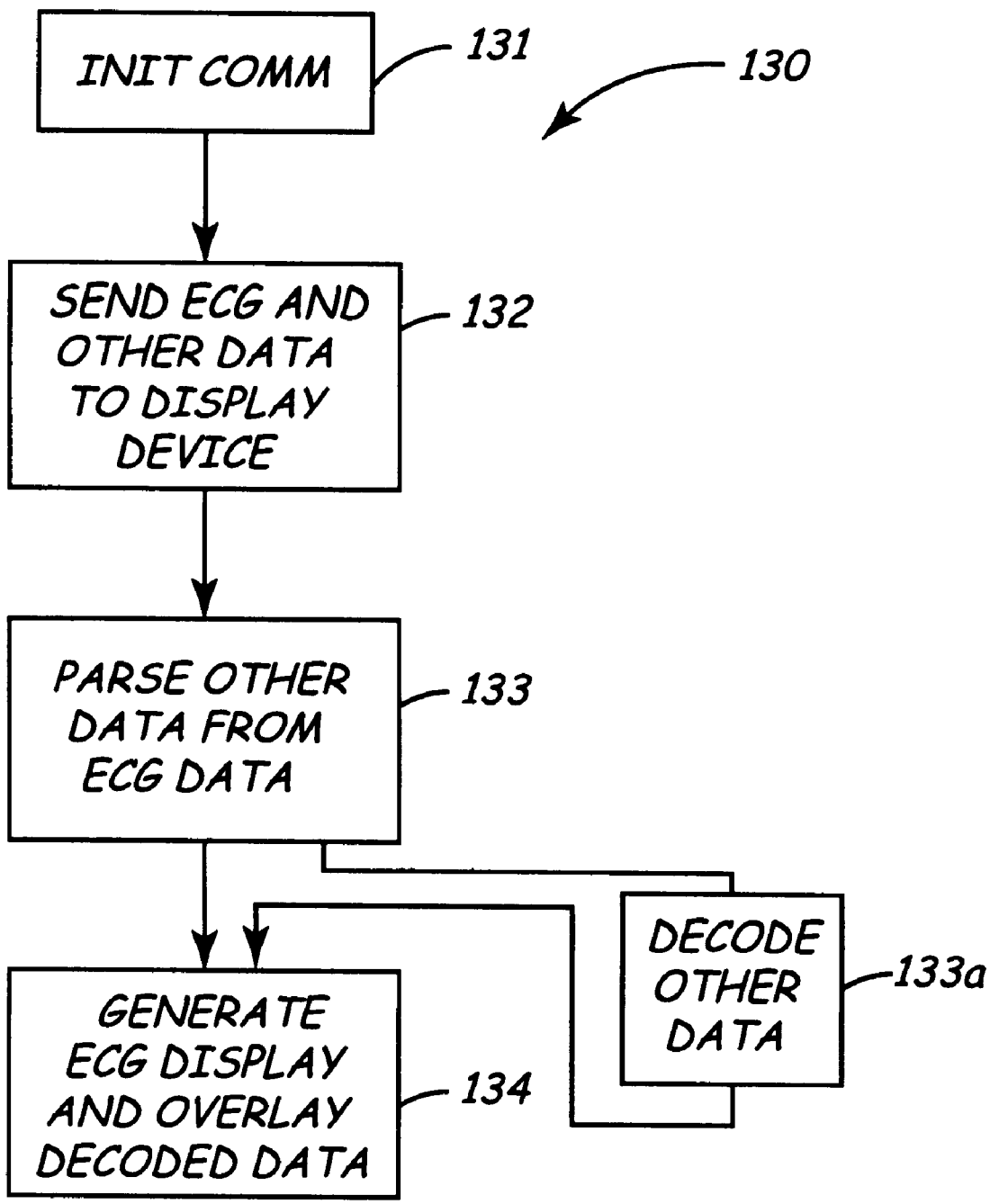
FIG. 13 is a flow chart of the process of transforming a data marker indicator signal into a display feature in accord with is invention.

The flow of data from the memory of the IMD to the display screen 96a of the programmer, or another device receiving the data, which may be downstream in the telecommunications network, is explained with reference to FIG. 13, via the flow chart 130. First, communications is be initiated in step 131, and the implanted device begins transferring ECG and other marker, indicator, or sensor data to the external device(s) in step 132. There must be a program in the external device that parses the other data from the ECG data in step 133. The data must then be decoded into the display icon or other display artifact appropriate to the other data, as shown in step 133a. Preferably, the external device will then generate a display of the ECG including the other data. This display may be similar to that shown in FIGS. 8A–9B. For example, a pressure wave signal that is recorded simultaneously with the ECG may be displayed with temporal alignment in the same window or in two aligned windows. Various representations of types of noise and types of auto-triggers are easily imagined within the scope of the invention. The external device may include a processing feature that displays and/or prints the ECG signal without the other data.

Figure 9A:
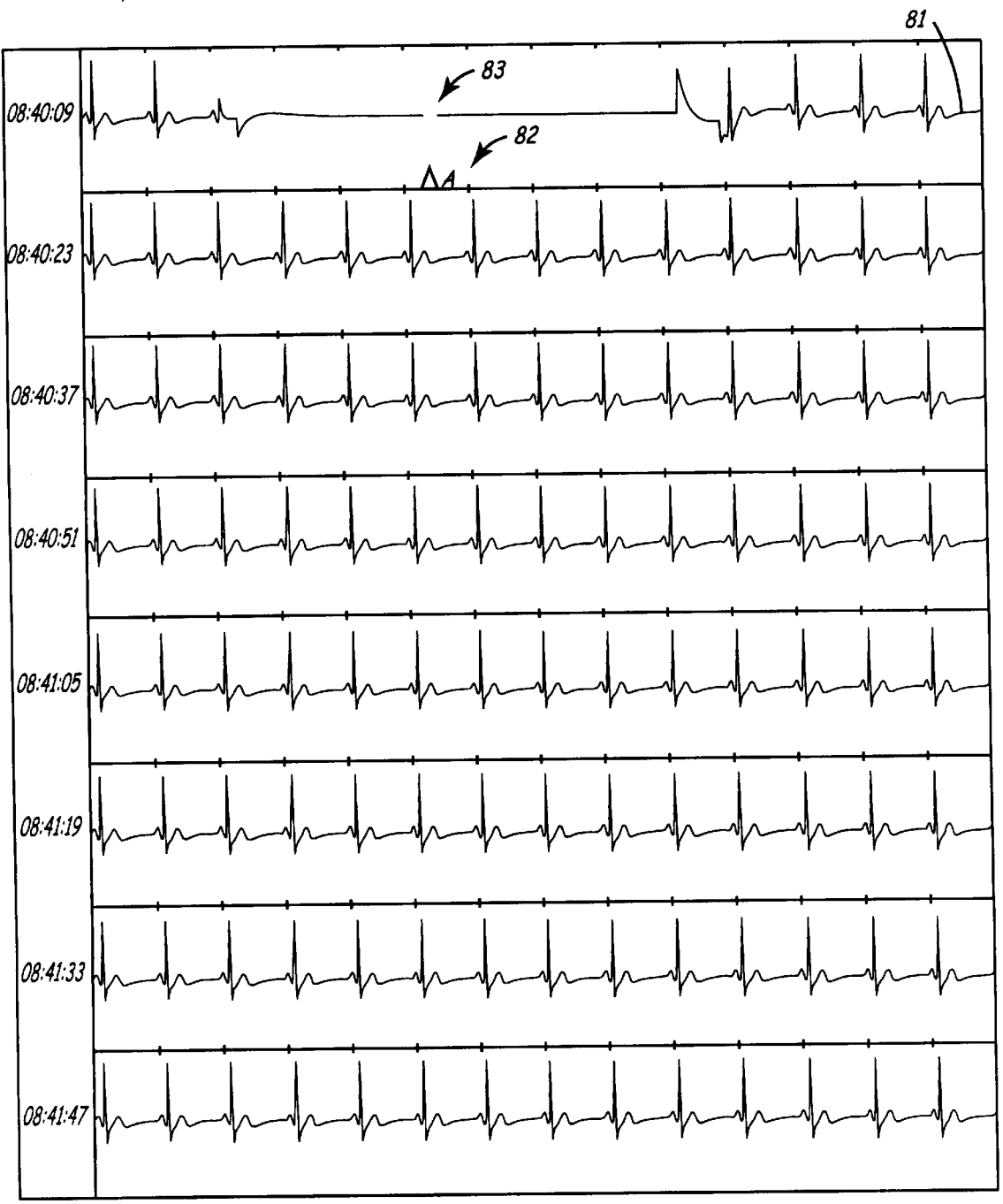
FIGS. 9A and 9B are rough representations of displays of an ECG segment for use with a preferred embodiment.
Figure 9B:
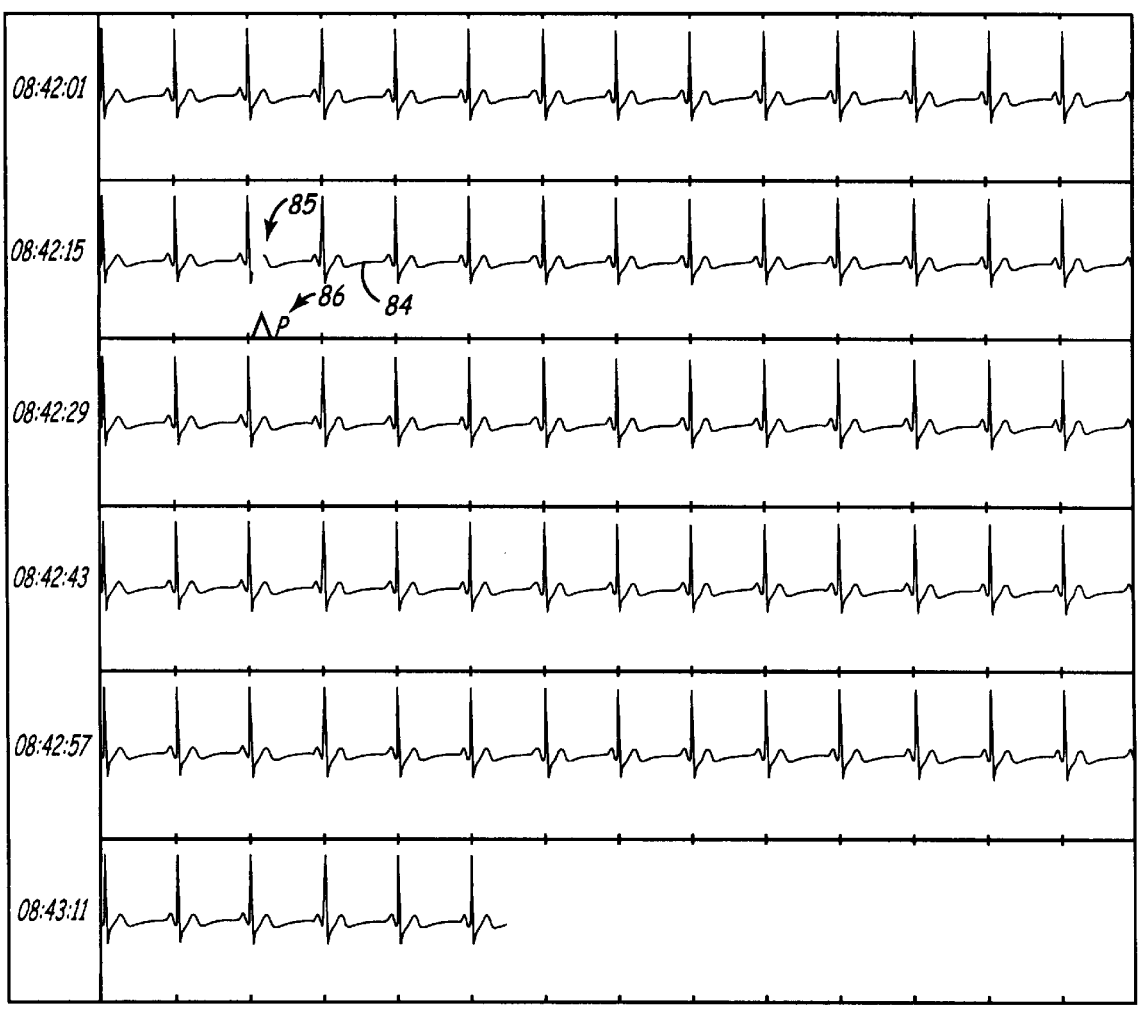

Thus, as a simple example, assume values 00 and FF (hex) indicate an automatic and manual activation, respectively. Thus, in FIG. 9a, the programmer 86 displays electrocardiogram 81 including a break 83 where the indicator of the automatic trigger 82 replaces some of the data. An intelligent interpolating program may fill the gap at 83. In FIG. 9b, a patient activation will be shown by the mark at 86 in line 84, and again with a gap at point 85.

Figure 8A:
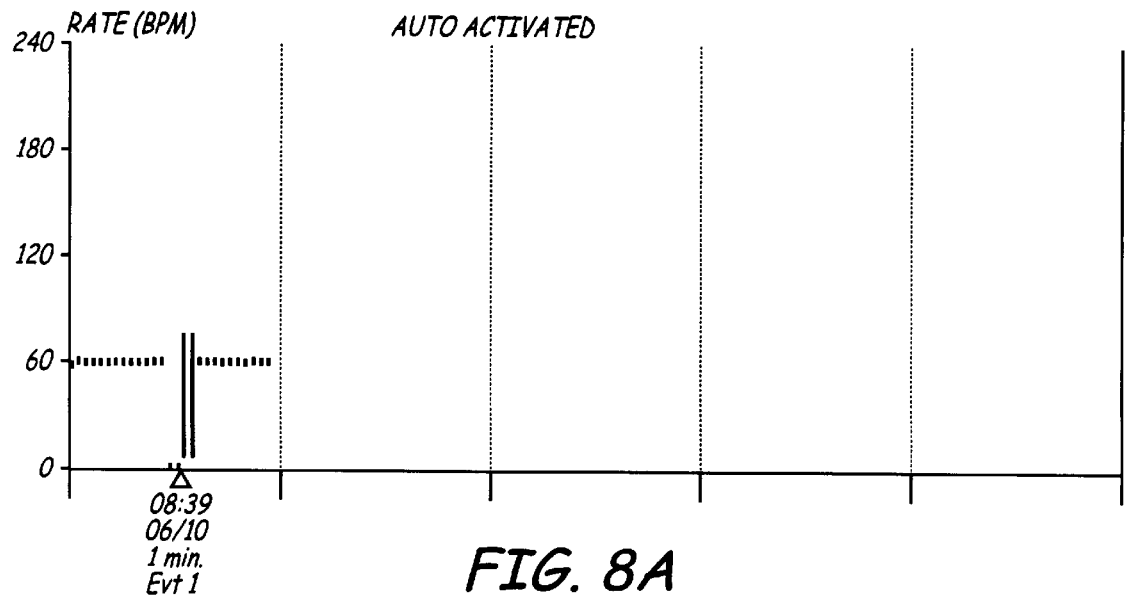
FIGS. 8A and 8B are rough representations of displays for use with a preferred embodiment.
Figure 8B:
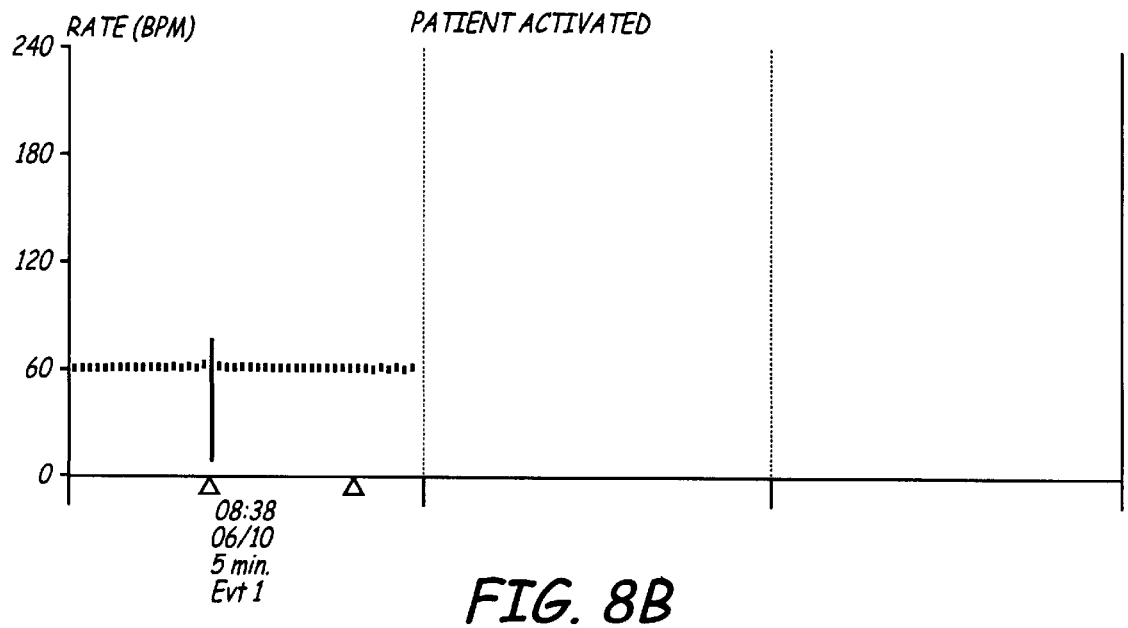

For ease in interpreting the data, a long-term rate graph can also be drawn as in illustrated in FIGS. 8a and 8b. Here, the position and height of the bars indicate the range of heart rate for the particular time of the bar, and the arrows indicate the automatic triggers.

Using more than just FF and 00 (say 00, 01, 02 and FA-FF), a larger number of values are unavailable to encode amplitude values, but can be used to provide indications of other types of useful information for interpreting the data including various types of noise, out-of-range sensor conditions, or an exact identifier for the particular type of arrhythmia or other auto-trigger which caused a particular segment of ECG to be stored.

ECG Recording Functionality for Preferred Embodiments

The most important function of the simple versions of this invention is the long term electrocardiogram (ECG) monitoring of the subcutaneous (intramuscular) ECG. The device continuously records and monitors the subcutaneous ECG in an endless loop of memory. In its primary mode, the device is triggered by the patient to save/retain in memory ECG data when the patient detects predetermined symptoms such as syncope or palpitations. The device may store data for a period of time both before, and/or after, the patient-activated trigger event. Patient activation may be performed using a small device that signals the implantable device from outside the body, as disclosed in co-pending U.S. application Ser. No. 09/033,678, incorporated herein by this reference.

In a preferred embodiment, 128 Kbytes of memory the device is provided to store 42 or 21 minutes of ECG, which can be reset after off-loading by telemetry to an external device for analysis and display. In one form there are four modes settable for the patient to trigger activation of data storage recording. In another embodiment, there are auto-triggers that automatically trigger the storage of data, which may include the trigger event and noise data. In the patient-activated trigger modes, the patient can capture either one or three events between off-loadings non-compressed data, or data the is compressed at a ratio of 1:2, or some other device-supported compression ratio. This is determined by the mode programmed by the physician or attendant. If greater detail of the triggered ECG is required than can be developed from compressed data storage, the physician can select non-compressed recording, thereby reducing the time available to record. In some embodiments, sample rate may be modified as well, but this is not preferred.

Compression is preferably done using a known compression algorithm implemented in hardware. Many types are known, and alternatively, software compression could be used. One exemplary data-independent compression scheme is described in the article "Arrhythmia Detection Program for an Ambulatory ECG Monitor" by Mueller, copyright 1978, ISA, ISBN 876645. Using this algorithm in one embodiment, a pre-trigger recording time has a maximum length of 2400 seconds, and a post-trigger recording time has a maximum length of 120 seconds. A higher sample rate (less compressed) rate of 1200 samples per 60 second may be used to record a single event, and a lower rate of 360 samples per 60 seconds may be used to record three events. These time values are obviously only examples and may be selected as appropriate within the ambit of this invention. After such samples are stored and the device memory locations are fill, older samples will be overwritten by the next triggered event, since in the preferred embodiment the memory is maintained in a continuous loop.

An implantable medical device with the invention may have several operating modes including pure auto-triggering, patient triggered only modes, and combination modes, if desired. It should be considered that with auto-triggered events, the determination by the device of an event worth recording and the subsequent activation of the trigger by the device itself will be faster than the patient finding his device for activation or otherwise activating the device, so the pre trigger time record for automatic triggered storage sequences or ECG segments can be smaller. In one preferred embodiment the memory is segmented to allow for 14 auto-triggers and 3 manual triggers. Further detail regarding modes is described with reference to FIGS. 11 and 12.

The patient activated triggering of a preserved form of the recorded ECG signal can be carried out by using a small hand-held external device which may be of any number of different forms. In one instance, a hand-held battery-powered device uses a coded radio-frequency telemetered signal through the skin to the device, and is activated by the press of a button. A less complex device involves a small hand-held mechanism that includes a magnet is used to close a magnetic switch within the implanted device. For example, the area of the body that has the implant may be tapped a predetermined number of times with the magnet to close the switch. Other methods for triggering ECG data retention in memory use physical tapping or slapping of the finger or hand on the skin over the device in a particular cadence and/or number of taps such that no external triggering device is needed. With such methods, the disadvantage is that the patient needs to memorize the triggering sequence. Matched voice activation with a known command is also possible. Another approach involves light activation through the skin using a light source and receiver. Auditory/sonic activation may be employed using a hand-held auditory/sonic source held over the skin with a microphone receiver in the device. Once disadvantage of all of these patient-activated mechanisms is that patient compliance is required. Thus, it may be desirable to incorporate an automatic activation mechanism with these mechanisms. This could include activation by automatic recognition of an arrhythmia, an abnormally fast or slow heartbeat, or for any other predetermined physiologic condition the device is capable of detecting.

If a patient trigger is used, it is advantageous to provide feedback to the patient regarding whether the attempt to trigger long-term storage of the event was successful. To accomplish this the implant should telemeter out a signal that indicates it has recognized a valid trigger. The external triggering device then notifies the patient via the triggering device or through some known alarm mechanism whether the implanted device has been properly triggered. This notification can be one of any combination of a number of feedback methods including: one or two visual sources such LED's, an auditory source such as a beeping speaker in one or two tones, or a tactile source such as a vibration. See also U.S. Pat. No. 5,518,001 (incorporated herein by this reference) for other potential trigger-indicator ideas for a hand-held patient activated trigger device.

Features and Construction of the Preferred Embodiment Implantable Devices

Figure 11:
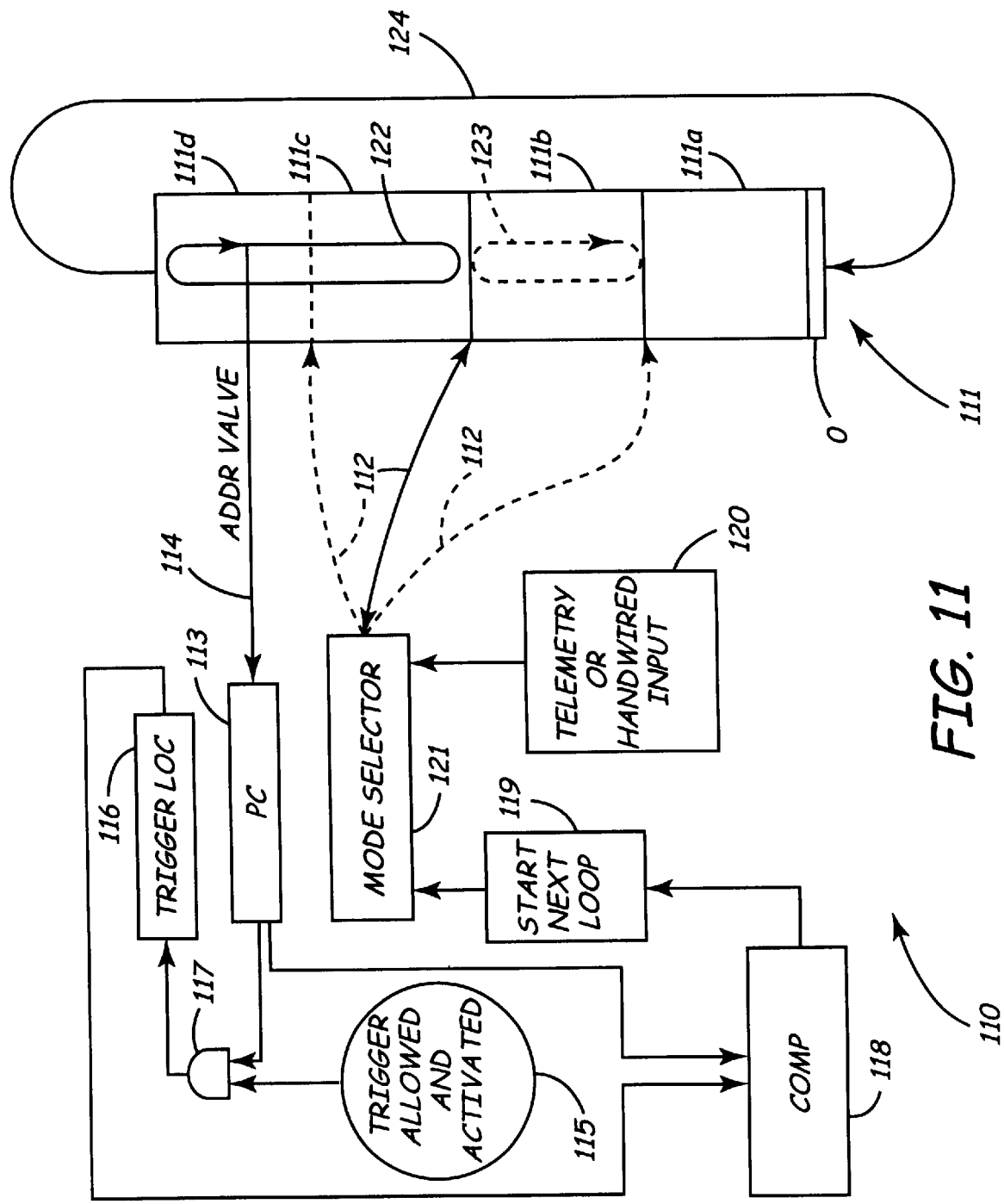
FIG. 11 is a block diagram of the looping memory and its control circuitry in accord with a preferred embodiment of the invention.

Referring now to FIG. 11 in which a block diagram of a functional model 110 of the controller and memory 111 of a preferred embodiment device is illustrated. The memory is generally organized as a continuous loop of, preferably, 8 bit addresses starting at address 0 and looping back around to address 0 through line 124. By telemetry or hard-wired input during manufacture 120, a mode selector 121 is set so as to divide the memory 111 into working segments 111a–d. The address of the start of each of these segments is indicated with lines 112.

Since this device is used for recording physiologic data, after the data is compressed, converted, formatted and is in appropriate digital form, it is continually recorded in the memory 111. The address value at the tip of arrow 122 in the combined memory space 111d, 111c is monitored by a program counter register 113.

The size of each memory segment set in a given mode limits the amount of data available for each triggered event. In the preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7, (the patent being incorporated herein by this reference in its entirety.

To use a single program counter the actual trigger address minus the time (in memory location storage events) required to have already stored the amount of data needed for pre event analysis for that trigger is stored as a value in the trigger location register 116 of FIG. 11. If a larger time for pre trigger recording is required by a trigger occurring during an already triggered event,(say, a manual trigger follows the occurrence of an auto-trigger), the value in the trigger register can be decrement, thus yielding a larger pre trigger time period in the allocated memory segment for this event. A priority system for whether to extend the pre trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto-triggered one because upon recovering from an event the patient has enough time to recover, get their wits about them, and find the triggering device. Manual triggering may therefore be set to record in double or multiple sized segments. FIG. 11's segments 111c and d are joined by looping arrow 122 to give effect to this concept.

Because the memory size is preferably quite limited, a time record or first-in-first-out pool record should be kept so that that the newest triggers record over the oldest event segments. An additional preferred feature allows for a mode that prevents recording over any triggered event segment. This is preferably implemented by a counter which increments for each segment used and has a limit for the number of available looping segments. When this counter reaches its limit, recording of new events is disabled.

When a trigger is activated, a recording of a signal is not disabled, a signal 115 is permitted by control gate 117 to allow the program counter address to be loaded into a trigger location address register 116. After loading, each subsequent clock cycle or set of clock cycles, as determined by the device configuration, will load the trigger location from 116 into a comparator 118 to compare this location with the program counter address stored in register 113. When comparator 118 detects a match, an appropriate output is generated to start the next loop via control circuit 119. This control circuit 119 will cause the mode selector to point to the next available loop location effectively placing that into the program counter 113.

Figure 12:
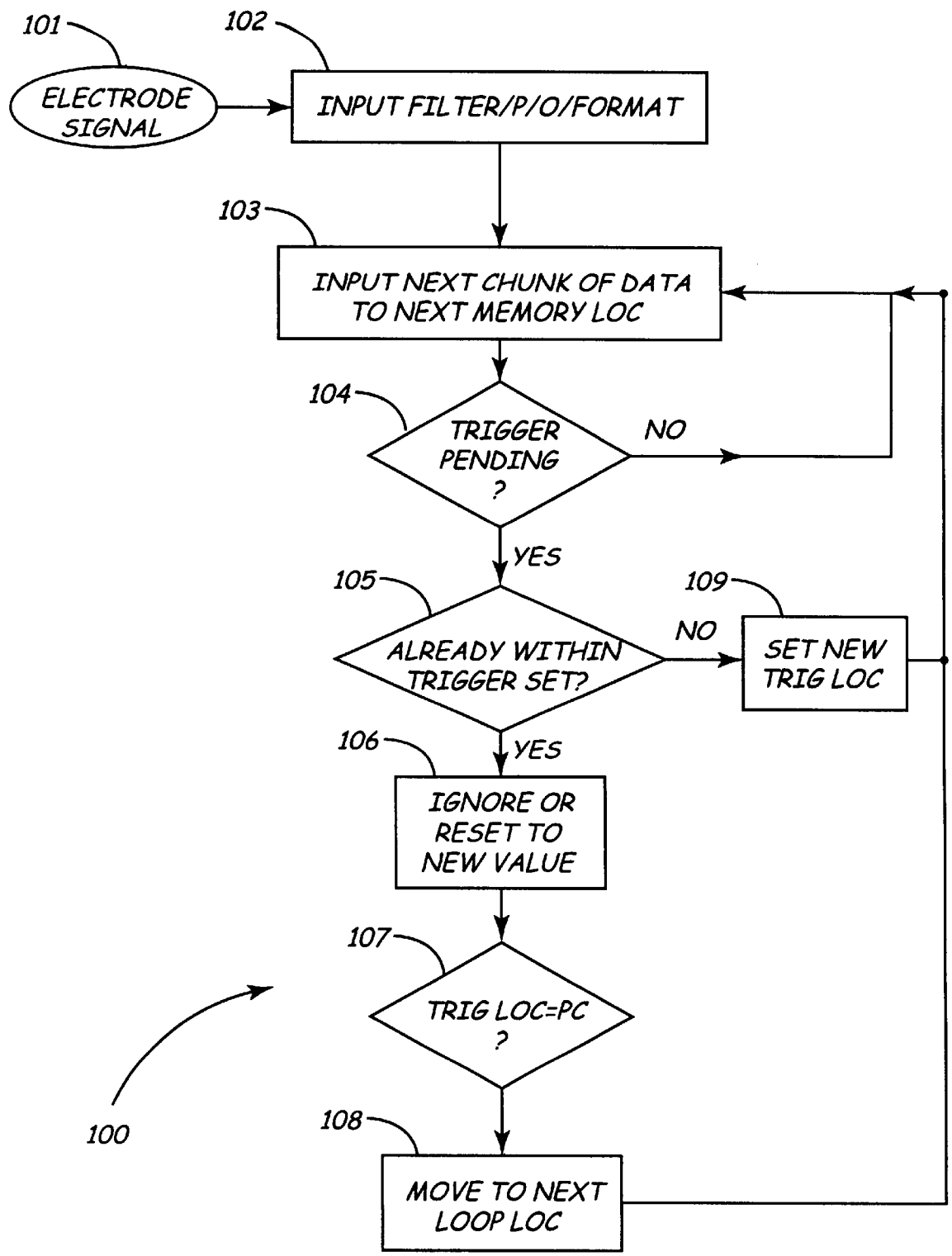
FIG. 12 is a flow chart of the functioning of the recordation of triggered events in a preferred embodiment of the invention.

The diagrammatic algorithm 100 to indicate the flow of this information is found in the illustration of FIG. 12, in which an electrode signal 101 is filtered, converted from analog input to digital values, compressed, and optionally formatted in step 102 so as to be in appropriate form to store in a memory location designated by a program counter pointer.

This data word format could contain a value representing compressed data at various available ratios, and may be nixed with other information like data provided by another sensor or a clock. The stored data may include information related to the signal taken at the sampling rate. Thus, lower sampling rates to save power will adversely affect the usefulness or detail of the data. Output from step 102 provides the next segment (which may be a word) of data to the next memory location in step 103.

The device determines whether any trigger pending after storing each segment of data in step 104. If not, the next segment of data is stored. If there is, the device preferably checks to see if there is another trigger already set and if so either ignores it or resets the value of the reserved looping memory area (like areas 111a–d in FIG. 11) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

It should be recognized that any of the inventive concepts taught herein may be applied to implantable devices to supplement their other functions, such as a supplemental recording system for a pacemaker, implantable drug pump, et cetera. Further, known enhancements to telemetric communication can be used to automatically activate off-loading of data to a device located in the patient's home. Such a device could send its received communications to the attending care giver/physician's office at some convenient time, telephonically or otherwise so as to enable close compliance with prescribed follow-up of patient conditions. This invention is not understood to be limited in scope except by the following claims.

What is claimed is:

1. An implantable medical device (IMD) comprising electrodes suitable for chronic contact with internal tissue in a living body so as to receive physiologically originated electrical signals via said contact, said IMD having a hermetically sealed housing and at least one conductor inside said housing, and wherein said electrodes are connected to provide said physiologically originated electrical signals to said at least one conductor inside said housing, said IMD further comprising:

an ECG sensing circuit inside said housing for receiving said physiologically originated electrical signals from said at least one conductor and for generating ECG sample signals having values representative of a feature in said physiologically originated electrical signals at a sampling rate;

an activation triggering circuit inside said housing also in electrical connection to said at least one conductor, for sensing a triggering event and for generating and providing as output, a trigger signal in the presence of triggering events;

a memory circuit connected to receive data signals and to store or retrieve said data signals under control of a processor circuit;

said processor circuit for reacting to said trigger signal to initiate storage into said memory of a group ECG sample signal in said ECG sample signals and said trigger signal such that said trigger signal replaces at least one of said group of ECG sample signals.

2. The IMD as set forth in claim 1 wherein said activation trigger circuit further comprises a noise sensing circuit in electrical connection to said at least one conductor, for sensing noise in said at least one conductor, and in response thereto, for generating a noise detection signal as said trigger signal if noise is sensed to be present in said at least one conductor.

3. The IMD as set forth in claim 2 further comprising an input amplifier circuit coupled to said ECG sensing circuit for generating apparent R-wave signals based on said physiologically originated electrical signals from said at least one conductor, and for generating apparent R-wave detection signals responsive thereto; and an auto-trigger circuit for detecting apparent arrhythmias based on said apparent R-wave detection signals from said input amplifier circuit.

4. The IMD as set forth in claim 2 further comprising an input amplifier circuit coupled to said ECG sensing circuit for generating apparent R-wave signals based on said physiologically originated electrical signals from said at least one conductor, and for generating apparent R-wave detection signals responsive thereto, and input amplifier circuit further being responsive to said noise detection signal to cancel generation of said apparent R-wave detection signals in the presence of said noise detection signals; and an auto-trigger circuit for detecting apparent arrhythmias based on said apparent R-wave detection signals from said input amplifier circuit.

5. The IMD as set forth in claim 1, and further comprising an R-wave detection circuit connected to said at least one conductor for sensing the presence of apparent R-waves in said physiologic signal and for generating an R-wave detect signal when apparent R-waves are sensed, and wherein said activation trigger circuit comprises a trigger sensing circuit coupled to receive said R-wave detect signal, and for generating an apparent arrhythmia signal as said trigger signal in the presence of a predetermined pattern of R-wave detect signals.

6. The IMD as set forth in claim 5, wherein said processor circuit includes means for receiving a manual trigger signal generated outside said living body, and in response thereto, for initiating storage into said memory of said group of said ECG sample signals.

7. The IMD of claim 6, wherein said processor in response to a manual trigger signal produces distinct data signal indicative of said manual trigger signal.

8. The IMD as set forth in claim 1, and further comprising:

an R-wave detection circuit connected to said at least one conductor for sensing the presence of apparent R-waves in said physiologic signal and for generating an R-wave detect signal when apparent R-waves are sensed, and wherein;

said activation trigger circuit comprises a trigger sensing circuit coupled to receive said R-wave detect signal, and for generating and providing as output, an apparent arrhythmia signal as said trigger signal in the presence of a predetermined pattern of sensed apparent R-waves; and a noise sensing circuit in electrical connection to said at least one conductor, for sensing noise in said conductor and for generating and providing as output, a noise detection signal if noise is sensed to be present in said at least one conductor, and wherein:

said processor circuit stores a data signal representative of said noise detection signal into said group of ECG sample signals.

9. The IMD as set forth in claim 1, and further comprising an additional physiologic sensor circuit comprising a physiologic sensor for measuring a physiologic a condition and an output generating circuit for generating an additional physiologic data signal output representative of said measurement of said physiologic condition, and wherein said processor circuit stores said additional physiologic data signal with said group of ECG sample signals.

10. The IMD as set forth in claim 1, wherein said processor circuit can only replace a predetermined number of said group of ECG sample signals with said memory trigger signal.

11. The IMD as set forth in claim 10, wherein said predetermined number is not more than 1 in a group of 30 ECG sample signals.

12. The IMD as set forth in claim 1, and further comprising signal to data conversion circuit means for generating a range of digital value data signals representative of said feature of said physiologic signal, wherein a portion of a said range is dedicated to storing signals indicative of said memory trigger signal and is unavailable for representing said feature.

13. The IMD as set forth in claim 1 wherein said feature is amplitude or a variation in amplitude.

14. A medical information system comprising the IMD as set forth in claim 1, wherein said IMD further comprises:

a telemetry circuit for sending and receiving telemetry data signals between itself and an outside device and further comprising:

said outside device having a telemetry circuit for receiving said telemetry data signals and having transformation circuitry for transforming said telemetry data signals into an image for display on a display screen, wherein said transformation circuitry reconstitutes said telemetry data as display data and wherein said transformation circuit parses said additional data from said ECG data in said reconstituted data for display of said ECG data as an ECG representation on said display screen.

15. An implantable medical device (IMD) for monitoring a physiological signal in a body, comprising:

a sensor to sense the physiological signal;

a sampling circuit coupled to the sensor to generate samples of the physiological signal;

a storage circuit coupled to the sampling circuit to selectively store ones of the generated samples in a time-ordered sequence;

a trigger circuit coupled to the storage circuit to generate a trigger signal in response to detection of a trigger event, the trigger signal to control the selective storage of the ones of the samples; and wherein the storage circuit includes circuits to store one or more data signals that are descriptive of the trigger signal such that ones of the generated samples are replaced by the one or more data signals in the storage circuit.

16. The IMD of claim 15, wherein the one or more data signals that are descriptive of the trigger signal are descriptive of a type of the trigger event.

17. The IMD of claim 15, wherein the trigger circuit includes a circuit to generate the trigger signal in response to a trigger event of noise in the physiological signal.

18. The IMD of claim 16, wherein the trigger circuit includes a circuit to generate the trigger signal in response to a trigger event that includes detecting a predetermined characteristic of the physiological signal.

19. The IMD of claim 15, and further including a noise detector circuit coupled to the trigger circuit to generate noise signals indicative of noise in the physiological signal, and wherein the storage circuit includes circuits to store the noise signals along with the ones of the samples.

20. The IMD of claim 19, wherein the noise detector circuit includes means for generating the noise signals to indicate a type of the noise detected in the physiological signal.

* * * * *

UNITED STATES PATENT AND TRADEMARK OFFICE
CERTIFICATE OF CORRECTION

PATENT NO. : 6,347,245 B1 Page 1 of 1
DATED : February 12, 2002
INVENTOR(S) : Brian B. Lee and Michael R. Kane It is certified that error appears in the above-identified patent and that said Letters Patent is hereby corrected as shown below:

<u>Column 16,</u>
Line 42, after "group" insert -- of said --.
Line 43, delete "signal" and insert -- signals --.
Line 43, delete "in" and insert -- and --.
Line 43, delete "ECG sample signals and said."
Line 45, after "one" delete "of" and insert -- ECG sample signal in --.

Signed and Sealed this

Eleventh Day of March, 2003

JAMES E. ROGAN
*Director of the United States Patent and Trademark Office*